(12) United States Patent
Lee

(10) Patent No.: US 10,324,060 B2
(45) Date of Patent: Jun. 18, 2019

(54) ANALYTE SENSOR

(71) Applicant: Senova Systems, Inc., Sunnyvale, CA (US)

(72) Inventor: Eric Lee, Sunnyvale, CA (US)

(73) Assignee: Parker-Hannifin Corporation, Cleveland, OH (US)

( * ) Notice: Subject to any disclaimer, the term of this patent is extended or adjusted under 35 U.S.C. 154(b) by 0 days.

(21) Appl. No.: 14/373,894

(22) PCT Filed: Jan. 24, 2013

(86) PCT No.: PCT/US2013/023029
§ 371 (c)(1),
(2) Date: Jul. 22, 2014

(87) PCT Pub. No.: WO2013/112767
PCT Pub. Date: Aug. 1, 2013

(65) Prior Publication Data
US 2015/0027887 A1    Jan. 29, 2015

Related U.S. Application Data

(60) Provisional application No. 61/590,636, filed on Jan. 25, 2012, provisional application No. 61/608,483, filed on Mar. 8, 2012.

(51) Int. Cl.
| | |
|---|---|
| *G01N 27/416* | (2006.01) |
| *G01N 27/30* | (2006.01) |
| *G01N 27/333* | (2006.01) |
| *G01N 27/28* | (2006.01) |

(52) U.S. Cl.
CPC ....... *G01N 27/4167* (2013.01); *G01N 27/286* (2013.01); *G01N 27/301* (2013.01); *G01N 27/302* (2013.01); *G01N 27/3335* (2013.01)

(58) Field of Classification Search
CPC .......... G01N 27/4166; G01N 27/4167; G01N 27/302; G01N 27/30; G01N 27/414–27/417; G01N 27/301; G01N 27/303; G01N 27/4117; G01N 27/4035; G01N 27/333

See application file for complete search history.

(56) References Cited

U.S. PATENT DOCUMENTS

| | | | |
|---|---|---|---|
| 639,515 A | 12/1899 | Brown | |
| 2002/0070112 A1* | 6/2002 | Lee | G01N 27/4035 204/431 |
| 2009/0099433 A1* | 4/2009 | Staib | A61B 5/14532 600/345 |
| 2011/0117477 A1* | 5/2011 | Pareek | G01N 21/4788 430/2 |
| 2011/0259092 A1 | 10/2011 | Yu et al. | |

(Continued)

FOREIGN PATENT DOCUMENTS

| | | | | |
|---|---|---|---|---|
| KR | 1020100036253 | | 4/2010 | |
| WO | US0026842 A1 * | | 9/2010 | ............. G01N 27/26 |

(Continued)

*Primary Examiner* — Gurpreet Kaur
(74) *Attorney, Agent, or Firm* — David Conklin; Kirton McConkie

(57) ABSTRACT

Matrix materials such polymers derivatives to contain a redox active material can be used to form electrodes and probes suitable for use in pH meters and other analyte sensing devices.

13 Claims, 23 Drawing Sheets

(56) References Cited

U.S. PATENT DOCUMENTS

| | | | | |
|---|---|---|---|---|
| 2012/0067745 A1* | 3/2012 | Duimstra | ............... | G01N 27/36 |
| | | | | 205/789 |
| 2012/0090995 A1* | 4/2012 | Leonard | ............. | G01N 27/4166 |
| | | | | 204/406 |
| 2012/0187000 A1* | 7/2012 | Kahn | ................. | G01N 27/3335 |
| | | | | 205/782 |
| 2013/0168609 A1* | 7/2013 | Lee | ...................... | G01N 27/302 |
| | | | | 252/500 |
| 2015/0114836 A1* | 4/2015 | Clark | ................... | G01N 27/302 |
| | | | | 204/403.02 |

FOREIGN PATENT DOCUMENTS

| | | | | |
|---|---|---|---|---|
| WO | US0028726 A2 * | 9/2010 | ............ | G01N 27/30 |
| WO | WO2010104962 | 9/2010 | | |
| WO | WO2010111531 | 9/2010 | | |

\* cited by examiner pH 7 reference solution:

| Analyte pH | PP (EWE) | PP (IWE) |
|---|---|---|
| 2 | -156 | -447 |
| 4 | -267 | -445 |
| 7 | -455 | -447 |
| 10 | -616 | -449 | pH 2 reference solution:

| Analyte pH | PP (EWE) | PP (IWE) |
|---|---|---|
| 2 | -168 | -152 |
| 4 | -273 | -152 |
| 7 | -479 | -154 |
| 10 | -624 | -152 | pH 10 reference solution:

| Analyte pH | PP (EWE) | PP (IWE) |
|---|---|---|
| 2 | -152 | -624 |
| 4 | -269 | -622 |
| 7 | -453 | -622 |
| 10 | -616 | -618 |

| Buffer pH | pH value | | | |
|---|---|---|---|---|
| | Time (days) | | | |
| | 0 | 1 | 2 | 3 |
| 2 | 2.0 | 2.0 | 2.0 | 2.0 |
| 7 | 7.0 | 6.9 | 7.0 | 6.9 |
| 11.8 | 11.8 | 11.6 | 11.7 | 11.5 |

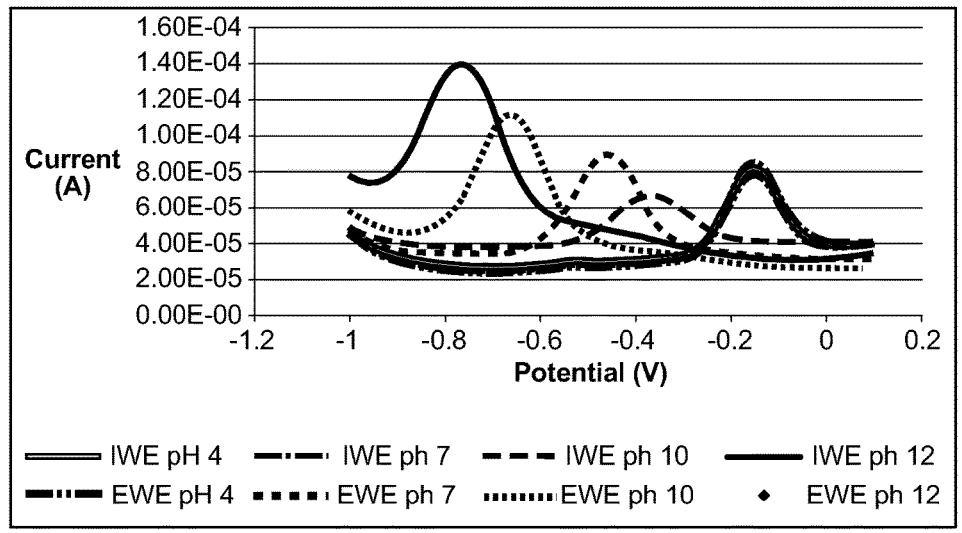
FIG. 21A
| | Peak potential at IWE (mV) | Peak potential at EWE (mV) | ΔPotential [IWE - EWE] (mV) |
|---|---|---|---|
| 4 | -148 | -294 | 143 |
| 7 | -150 | -488 | 339 |
| 10 | -147 | -670 | 518 |
| 12 | -144 | -761 | 615 |
FIG. 21B
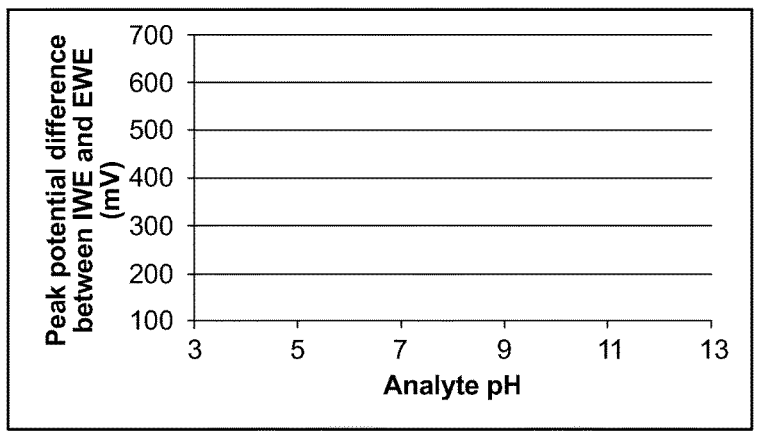
FIG. 21C

| pH | IWE peak position (mV) | WE peak position (mV) | Difference (mV) |
|---|---|---|---|
| 2.04 | -463 | -112 | -352 |
| 3.96 | -464 | -238 | -227 |
| 7.02 | -465 | -431 | -33 |
| 8.87 | -464 | -507 | 43 |
| 9.99 | -464 | -603 | 139 |
| 10.88 | -464 | -648 | 184 |
| 11.65 | -464 | -690 | 226 |

FIG. 22

ANALYTE SENSOR

This application is a National Stage of International Application No. PCT/US2013/023029, filed Jan. 24, 2013, and entitled ANALYTE SENSOR, which claims the benefit of United States Provisional Application Nos. 61/590,636, filed Jan. 25, 2012 and 61/608,483, filed Mar. 8, 2012. This application claims priority to and incorporates herein by reference the above-referenced application in its entirety.

BACKGROUND OF THE INVENTION

The present invention relates generally to technology for detecting an analyte. In various embodiments, the invention relates to devices for measuring pH, the potential of hydrogen, which is a measure of the acidity or alkalinity of a solution. The pH of a solution is determined by the concentration of dissolved hydrogen ions ($H^+$) (also referred to as hydronium ions, $H_3O^+$) within the solution. As the concentration of dissolved hydrogen ions within the solution increases, the solution becomes more acidic. Conversely, the solution becomes more basic as the concentration of dissolved hydrogen ions within the solution decreases. The concentration of dissolved hydrogen ions within a solution has traditionally been measured with a glass electrode connected to an electronic meter that displays the pH reading. Traditionally the terms "probe" and "electrode" have been used interchangeably to describe a functional grouping of component electrodes. As used herein, the term "electrode" is used to refer to a specific electrode in a probe, i.e., such as a "working electrode", a "reference electrode", or a "counter electrode", and "probe" refers to a functional grouping of electrodes sufficient to generate a signal that can be processed to generate a reading indicative of the concentration of an analyte of interest in a solution.

The traditional glass pH probe has a working electrode (WE) that is an ion-selective electrode made of a fragile, doped glass membrane sensitive to hydrogen ions. The pH-responsive glass membrane is the primary analyte sensing element in this type of probe and so is referred to as the "working" electrode. Hydrogen ions within the sample solution bind to the outside of the glass membrane, thereby causing a change in potential on the interior surface of the membrane. This change in potential is measured against the constant potential of a conventional reference electrode (RE), such as an electrode based on silver/silver chloride. The difference in potential is then correlated to a pH value by plotting the difference on a calibration curve. The calibration curve is created through a tedious, multistep process whereby the user plots changes in potential for various known buffer standards. Traditional pH meters are based on this principle.

The response of traditional glass working electrodes (and probes and meters containing them) to pH is unstable, and glass probes periodically require careful calibration involving tedious, time-consuming processes, multiple reagents, and a trained operator. The special properties and construction of the glass probes further require that the glass membrane be kept wet at all times. Thus, routine care of the glass probe requires cumbersome and costly storage, maintenance, and regular calibration performed by a trained operator to ensure proper working performance.

In addition to tedious maintenance and storage requirements, traditional glass probes are fragile, thereby limiting the fields of application of the glass probe. In particular, the fragile nature of the glass probe makes it unsuitable for use in food and beverage applications, as well as use in unattended, harsh, or hazardous environments. Accordingly, there is a need in the art for pH probes and meters (as well as other analyte probes and meters) that address and overcome the limitations of traditional pH probes and meters employing the glass probe.

In response to the limitations described above for traditional glass probe pH measuring systems, voltammetric systems were proposed to offer a more robust system for the determination of pH. In a voltammetric system, an electrical potential is applied in a controlled manner, typically varied linearly with time, and the corresponding current flowing through a conductive material is monitored by means of, for example, a potentiostat (see, for example, Wang, "Analytical Electrochemistry," $3^{rd}$ ed, John Wiley & Sons, 2006). Initial proposals (see U.S. Pat. No. 5,223,117) were based on the concept of a WE composed of a conductive substrate with a redox active molecule attached to its surface. The hypothesis was that, provided an appropriate "analyte-sensitive", redox active material (ASM) was used, the potential at which the maximum current flows in this system would be a function of the pH of the analyte solution. However, this initial proposal met with little enthusiasm, perhaps because it was demonstrated with an electrode that used gold as a substrate.

Significant advances were made in both theory and research laboratory practice of voltammetry-based analyte sensing systems when researchers discovered that carbon could replace gold as the conductive substrate and, moreover, that, regardless of the substrate, mixtures of redox active materials could be used in voltammetric systems (see PCT Pub. Nos. 2005/066618 and 2005/085825). One particularly intriguing proposal by these researchers was that a mixture of "analyte-sensitive" redox active materials (ASMs) and "analyte-insensitive" redox active materials (AIMs) could be attached to a conductive substrate and effectively convert it into both a WE (signal generated by the ASM) and a reference electrode (RE) (signal generated by the AIM). No significant advances, however, in either theory or practice were made for some time after these initial proposals and research (see, e.g., PCT Pub. Nos. 2007/034131 and 2008/154409).

The next significant advance in the field occurred when scientists discovered that, in practice, no redox active material is completely "analyte-insensitive" and that practical application of voltammetric technology should focus on WEs without AIMs. These scientists also discovered, however, that, regardless of whether a redox active material was characterized as an ASM or AIM (collectively referred to herein as "redox active materials" or "RAMs"), it could be made truly analyte-insensitive by sequestration in an ionic medium. This discovery led to the analyte-insensitive electrode or AIE, which could not only be used as a replacement of the conventional RE in traditional pH measuring systems but could also be used with WEs based on voltammetry. See PCT Pub. No. 2010/104962. Soon after these discoveries, pH meters suitable for use on the laboratory bench-top and for important research and development applications were created. See PCT Pub. Nos. 2010/111531 and 2010/118156. Later advances included the development of polymers with RAMs covalently attached thereto, as described in PCT Pub. No. 2012/018632.

However, despite these highly promising advances, in practice, the performance of these probes needed improvement in a number of aspects. First, robust and affordable devices incorporating them were needed. Second, significant advantages could be realized if there were a means to replace the conventional glass electrode of a conventional pH meter with a voltammetric probe. Third, there is a continuing need for improved access and utilization of measurement results through modern data processing means and devices such as computers, smartphones, controllers, and related instrumentation and control technology using wired or wireless systems and protocols. Fourth, reference electrodes with improved resistance to drift and reduced maintenance requirements prevalent in conventional reference electrode systems would be beneficial. Fifth, optimal methods and compositions for fixing redox active materials to the conductive substrate of an electrode for use in a voltammetry-based analyte-sensing system and for electrodes, probes, pH meters, and other analyte sensing devices based on voltammetric systems are needed that provide longer useful lifetimes and can be used for a wider variety of applications. Sixth, there is a need for electrodes for use in voltammetric applications that can be stored dry, particularly ones comprising wet-dry reversible reference electrodes. The present invention meets these needs.

SUMMARY OF THE INVENTION

The present invention relates generally to voltammetric electrodes and sensors and methods and materials for construction of their various components, including working and reference electrodes. The present invention also provides methods for immobilizing a redox active material in a conductive substrate, compounds, and compositions useful in the method, electrodes produced by the method, and pH meters and other analyte sensing devices incorporating one or more electrodes of the invention.

In some embodiments, the present invention provides a voltammetric sensor capable of communicating with a mobile or remote computing device, said sensor comprising: a working electrode, a reference electrode, a counter electrode, firmware and electronics for voltammetry and signal processing with optional local display and control, and a communications interface. The communications interface can be linked by a wire or by wireless communications to the mobile or remote computing device, which comprises a communications interface compatible with that of the sensor and software for display, recording, archiving, or further processing of pH (or other analyte concentration) and related information including, but not limited to, temperature.

In other embodiments, the invention provides a voltammetric sensor for use in conjunction with conventional pH meters as a universal replacement of the glass probe. This voltammetric sensor comprises an emulator, which may be referred to herein as a "universal potentiometry emulator", that converts the electronic signal output representing the measured pH value into a corresponding potential that a conventional pH meter can accept, process, and display.

Further, in some embodiments the invention provides a reference electrode with superior stability and independence from analyte concentration, and obviates the frequent and operator-dependent maintenance necessary with conventional reference electrodes.

Further still, in some embodiments the invention provides working electrodes exhibiting precise, reproducible response over a broad range of analyte concentration, especially that of the hydronium ion, by means of immobilizing analyte-sensitive molecules to a conductive substrate by physicochemical means, including covalent attachment and physical entrapment. The invention provides methods for immobilizing RAMs in a matrix that can be coated on the surface of a suitable substrate to form a redox active surface or can be directly molded to form a redox active substrate for use in analyte-sensing electrodes, probes, and sensors, such as pH meters and other analyte-sensing devices. The method is generally applicable to any redox active material, but in many embodiments, the method is practiced using the AIMs or ASMs known to be useful in voltammetry-based analyte-sensing methodology. In the method, the RAM is covalently attached to or non-covalently entrapped within the polymer that forms the matrix. In some embodiments, the RAM is first covalently attached to a monomer that is then polymerized to form the matrix material. In other embodiments, the RAM is admixed with one or more monomers and optionally other additives that are then polymerized to form a matrix material within which the RAM is entrapped or immobilized. In other embodiments, the RAM is covalently attached to or admixed with a polymer that may be used directly or cross-linked and then used. Variations and combinations of these embodiments are also provided.

In other embodiments, the invention relates to electrode components, electrodes, probes, and meters comprising one or more matrix materials of the invention. In some embodiments, the invention provides a working electrode that contains a matrix material of the invention comprising an ASM coated on an electrically conductive substrate such that it remains in electrical contact with the substrate. In other embodiments, the invention provides a working electrode that is directly molded from a matrix material of the invention comprising an ASM (i.e., there is no separate substrate, although there may be non-conductive materials that serve to support the electrode structurally). The present invention also provides sensors such as pH meters and other analyte sensing devices comprising such WEs. In some embodiments, the matrix material in these WEs can also have one or more AIMs attached to them. In other embodiments, the invention provides an AIE that contains a matrix material of the invention comprising either an ASM or AIM or both. In any of these embodiments, the matrix material of the invention can be coated onto the surface of a distinct electrically conductive substrate to form an electrode (or component thereof) or can be molded to form the electrode (or component) directly.

BRIEF DESCRIPTION OF THE DRAWINGS

FIGS. 21A-21C provide various tables and graphs which display results from tests using a voltammetric sensor cartridge in accordance with a representative embodiment of the present invention.

FIG. 22 is a chart displaying the test results of a voltammetric sensor cartridge in accordance with a representative embodiment of the present invention.

DETAILED DESCRIPTION OF THE INVENTION

Figure 1:
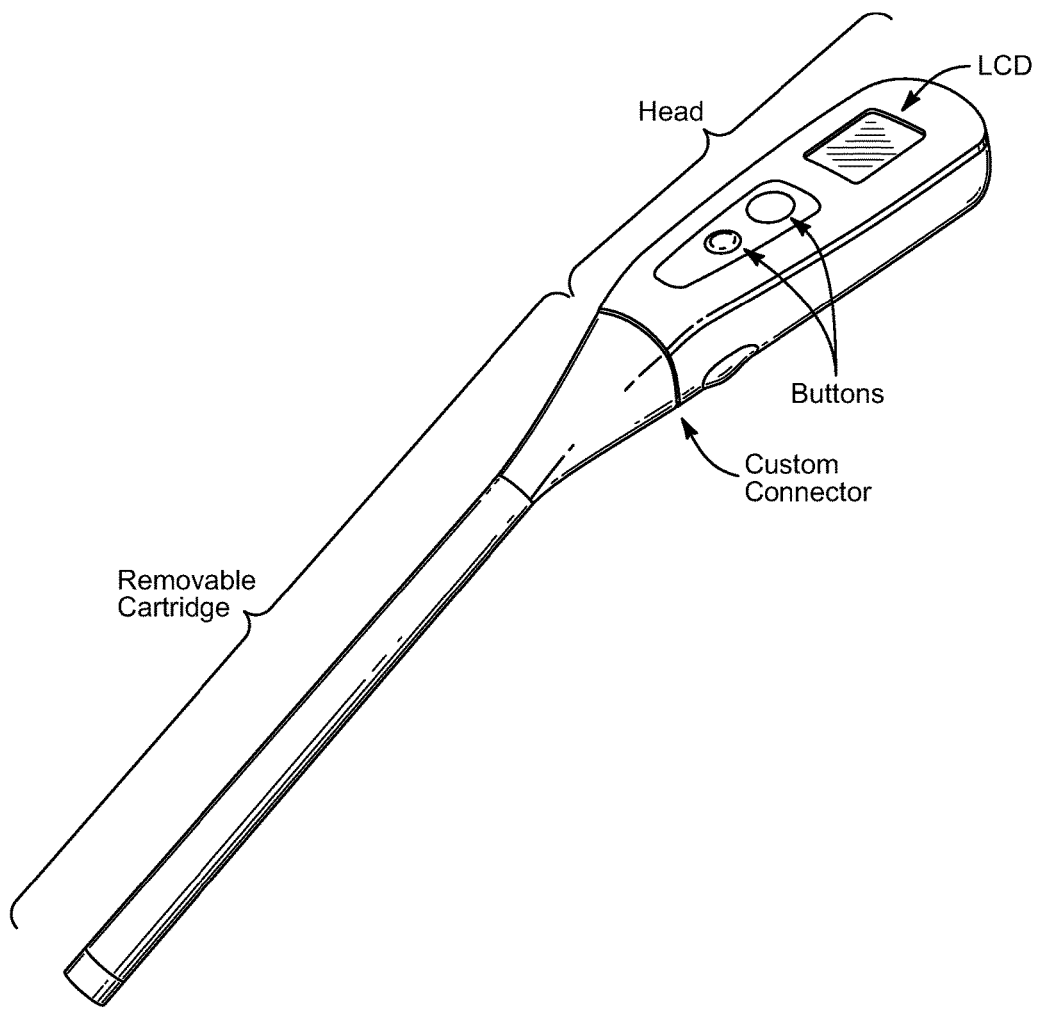
FIGS. 1 through 3C show a hand-held instrument comprising a voltammetric sensor in accordance with various representative embodiments of the present invention.
Figure 2:
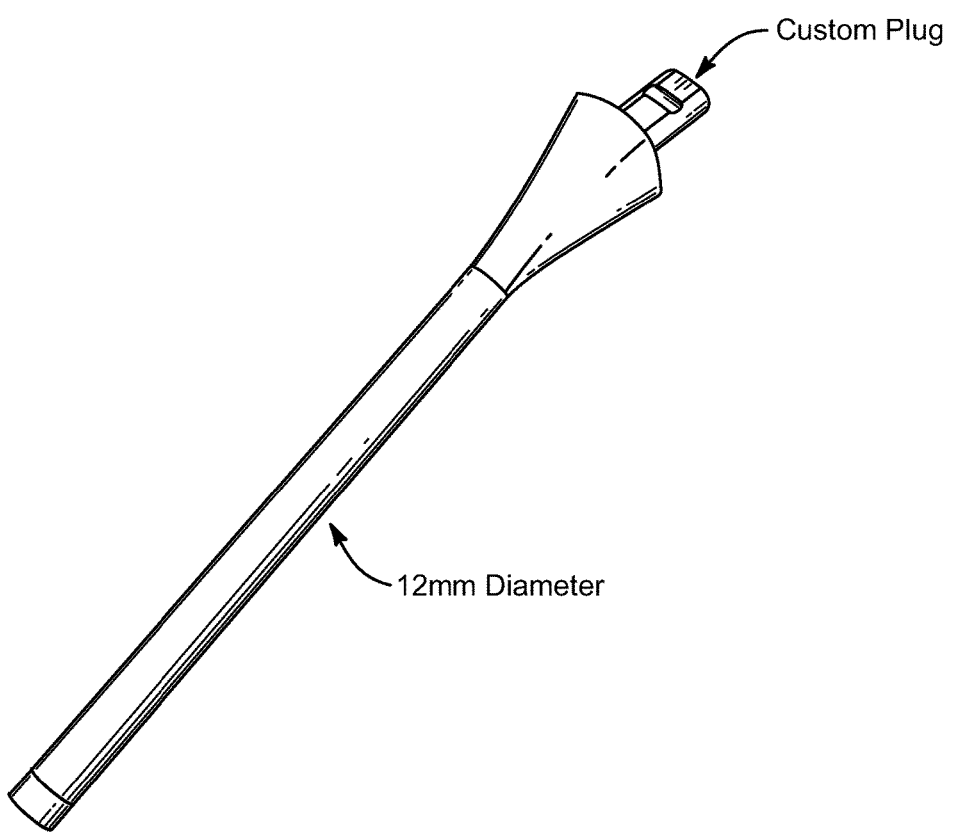
Figure 3A:
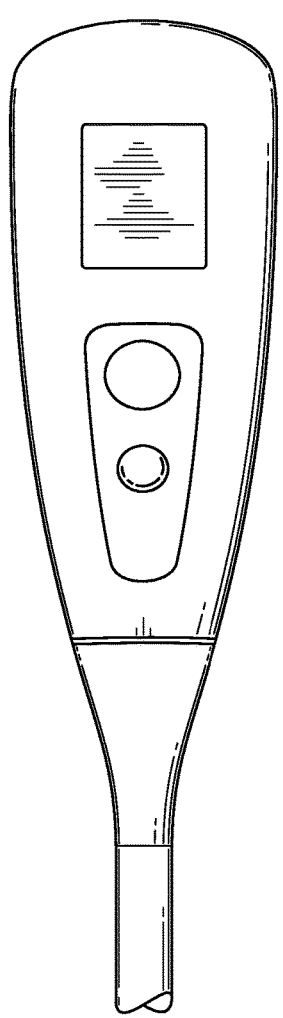
Figure 3B:
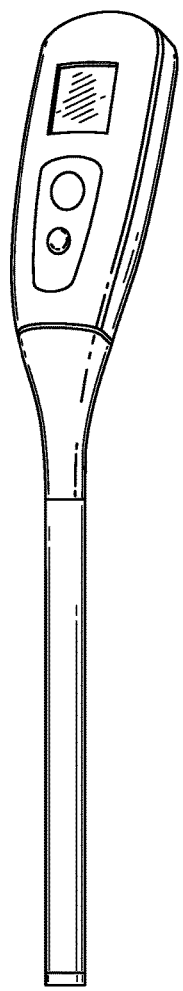
Figure 3C:
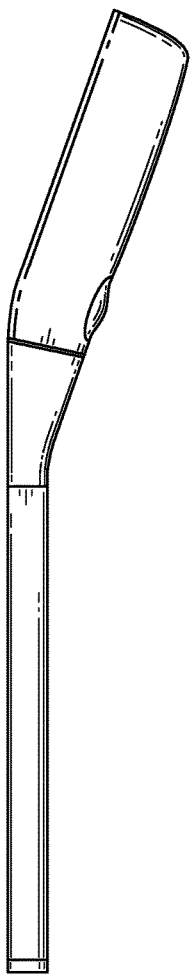

The present invention provides compounds, compositions, methods, electrodes, and sensors, including solid state analyte sensors, superior to those currently known in the art. The invention is described in detail below, and the detailed description is divided into sections for the convenience of the reader. Section 1 provides definitions. Section 2 describes the voltammetric sensors of the invention used in a self-contained, optionally hand-held, instrument, or whose output is transmitted through a wired or wireless connection to other computer devices and systems for display, storage, or further processing. Section 3 describes a voltammetric sensor of the invention that is a substitute for the glass probe and compatible with potentiometric pH measurement devices that utilize glass probes. Section 4 describes improved reference electrodes of the invention. Section 5 describes improved working electrodes of the invention.

Section 1. Definitions

As used in the specification and the appended claims, the singular forms "a," an" and "the" include plural referents unless the context dictates otherwise. Thus, for example, reference to "a binder" includes a composition of only a single binder and compositions that are mixtures of binders.

"Alkanyl" refers to a saturated branched, straight-chain or cyclic alkyl group. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, and the like.

"Alkenyl" refers to an unsaturated branched, straight-chain or cyclic alkyl group having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, and the like.

"Alkoxy" by itself or as part of another substituent refers to a radical —$OR_{100}$ where $R_{100}$ represents an alkyl group as defined herein. Representative examples include, but are not limited to, methoxy, ethoxy, propoxy, butoxy, and the like.

"Alkyl" refers to a saturated or unsaturated, branched, straight-chain or cyclic monovalent hydrocarbon group derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. The expression "lower alkyl" refers to alkyl groups comprising from 1 to 8 carbon atoms.

"Alkynyl" refers to an unsaturated branched, straight-chain or cyclic alkyl group having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, butynyls such as but-1-yn-1-yl, but-1-yn-3-yl, but-3-yn-1-yl, and the like.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. The aryl group may be, for example, ($C_5$-$C_{14}$) aryl, including but not limited to ($C_5$-$C_{10}$). Illustrative aryls include cyclopentadienyl, phenyl and naphthyl.

"Arylalkyl" refers to an acyclic alkyl group in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In preferred embodiments, the arylalkyl group is ($C_6$-$C_{20}$) arylalkyl, e.g., the alkanyl, alkenyl or alkynyl moiety of the arylalkyl group is ($C_1$-$C_6$) and the aryl moiety is ($C_5$-$C_{14}$). Illustrative embodiments include the arylalkyl group ($C_6$-$C_{13}$), e.g., the alkanyl, alkenyl or alkynyl moiety of the arylalkyl group is ($C_1$-$C_3$) and the aryl moiety is ($C_5$-$C_{10}$).

An "analyte" is a chemical species of interest present in a sample, the presence of which is detectable or the concentration of which is measurable using an analyte sensor system that incorporates a working electrode.

An "analyte-sensitive material" or "ASM" is a redox-active material that is sensitive or substantially sensitive to the presence or concentration of an analyte in a sample within those user-defined application-specific tolerances. "Substantially sensitive" to an analyte is used to mean sensitive within the tolerances required for a given application, as those tolerances are defined by an end user.

An "analyte-insensitive material" or "AIM" is a redox-active material that is insensitive or substantially insensitive to the presence or the concentration of an analyte in a sample. "Substantially insensitive" to an analyte is used to mean insensitive within the tolerances required for a given application, as those tolerances are defined by an end user.

An "analyte insensitive electrode" (AIE) is a special case of a reference electrode where the current flow depends in part on redox processes that are independent of the presence or concentration of species (apart from a minimum threshold of supporting electrolyte) in the sample composition including but not limited to the analyte. The AIE serves to provide a response that does not vary across time or sample composition and therefore can be used as an internal standard or 'zero point' to which the WE response may be compared. See PCT Pub. No. 2010/104962, incorporated herein by reference. An AIE contains one or more RAMs in electrical contact with a conductive substrate, a pseudo reference electrode (PRE, as defined below), and a means to place the RAM and often the PRE in a constant chemical environment isolated from, but in electrical and fluid communication with, an analyte solution. The conductive substrate and RAM of an AIE may be referred to herein as an "internal working electrode" or "IWE". As used herein, AIE can, depending on context, refer to the integrated functional unit (IWE, constant chemical environment, and PRE) or to the IWE or only to the matrix material component of the IWE. In the context of the current invention, a constant chemical environment is a buffer material that resists change in hydronium ion or hydroxide ion, i.e. pH, such that the RAM outputs a stable, reproducible voltammetric signal. Buffer solutions are the simplest form of constant chemical environment. ASMs of the current invention respond precisely to the formulation of buffered materials, which may include various buffered solids and semi-solids, buffered solutions, and buffer solutions. This characteristic leads to the deliberate use of a buffered material to produce a signal even more stable than conventional reference electrodes such as Ag/AgCl/KCl. The design and implementation of materials to create constant chemical environments are detailed below. Significantly, a constant chemical environment used in conjunction with an AIM such as ferrocene overcomes two shortcoming of that compound, namely: 1) its propensity to respond slightly to changes in analyte pH despite expectations to the contrary; and 2) the limited pH range (ca. 4 or above) for which ferrocene responds with a usable voltammetric signal.

An "analyte sensing device" is a sensor, a means to measure the signal from the sensor, and optionally a means to display that signal. A pH meter is a type of analyte sensing device. Thus, in some embodiments, an analyte sensing device includes a controller/processor unit, associated programs and algorithms, and a probe.

A "counter-electrode" or "CE," also sometimes referred to as an "auxiliary electrode," is an electrode that is required, in some analyte sensors, to pass current through the electrochemical cell to complete the electrical circuit. The CE serves as a source or sink of electrons and allows current to flow through the WE to effect the redox reaction. To avoid unwanted electrochemical redox processes occurring at the CE, which may interfere with the signal measured at the WE, CEs are typically made using relatively chemically inert materials, commonly platinum (Pt), but carbon allotropes are also commonly employed. Certain other metals may also be used, especially those exhibiting stability in harsh environments. Examples include, but are not limited to, gold, stainless steel, titanium, and specialty alloys.

"Coaxial" refers to a common axis about which various components, for example, electrodes, are positioned. In some embodiments, "coaxial" refers to a radial symmetry of concentrically or approximately concentrically positioned components. In some embodiments, the term "coaxial" refers to one or more electrodes being concentrically positioned within an outer or externally positioned electrode component; for example and without limitation, a WE, CE, and RE are coaxially positioned when the CE is the outer ring of a sensor tip that is immersed in the analyte solution, the WE is in the middle of the tip, and the RE is interposed between CE and the WE. See PCT Pub. No. 2010/111531, incorporated herein by reference.

"Dispersed" or "associated" in reference to a material, means that it is dissolved in a solution or suspended as a colloid, in a gas, liquid or solid. The term also encompasses embodiments in which the material is covalently bound to the surface of a solid or to a component of the solid. The term also encompasses embodiments in which the material is incorporated as a dopant in a crystal lattice. The term also encompasses materials intercalated within a solid.

An "electrode" is a component of a probe.

A "pseudo-reference electrode" or "PRE" is a type of electrode in the category of electrodes whose potentials vary predictably in accordance with the conditions of their environments. Once established, such correlation may be used to calculate an electrode potential for known conditions even if those conditions go beyond the relatively narrow range in which conventional reference electrodes are applicable, for example non-aqueous solutions or temperatures far from ambient. In those situations they provide a reasonably constant potential over the timescale of an electrochemical experiment, and the absolute potential of the PRE can be back-calibrated to a RE if required. Pseudo-reference electrodes typically do not comprise both halves of a redox couple. One example of a PRE is a silver wire (used commonly in non-aqueous electrochemistry). More recently, PREs have been used as a component of an AIE.

A "redox-active material" is a compound or composition that may be oxidized and reduced. "Redox activity" refers to either or both of those processes.

A "reference electrode" (RE) is an electrode used to establish the potential difference applied to the WE. Conventional REs have a certain fixed chemical composition and therefore a fixed electrochemical potential, thus allowing measurement of the potential difference applied to the WE in a known, controlled manner. An RE typically comprises two halves of a redox couple in contact with an electrolyte of fixed chemical composition and ionic strength. Because both halves of the redox couple are present and the composition of all the species involved is fixed, the system is maintained at equilibrium, and the potential drop (i.e., the measured voltage) across the electrode-electrolyte interface of the RE is then thermodynamically fixed and constant. For example a commonly used RE system is the Ag/AgCl/KCl system with a defined and constant concentration of KCl. The two half-cell reactions are therefore: $Ag^+ + e^- \rightarrow Ag$; and $AgCl + e^- \rightarrow Ag + Cl^-$. The overall cell reaction is therefore: $AgCl \rightarrow Ag^+ + Cl^-$ for which the Nernst equilibrium potential is given as: $E = E_0 - (RT/F)*\ln[Cl^-]$, where E is the measured RE potential, $E_0$ is the standard potential of the Ag/AgCl couple vs. the standard hydrogen electrode with all species at unit activity (by convention the standard hydrogen electrode is defined as having a potential of 0.0V); and R, T, and F are the universal gas constant, temperature, and Faraday constant, respectively, in appropriate units. Hence, the potential of this system depends only on the concentration (more strictly speaking the activity) of $Cl^-$ ion present, which, if this is fixed, provides a stable, fixed potential. Many other RE systems are known in the art. It is imperative that the composition of the RE remains constant, and hence almost no current should be passed through the RE (otherwise electrolysis will occur and the composition of the RE will change), which necessitates the use of a third electrode, the counter electrode (CE), to complete the circuit. However, two-electrode configurations can be used in the special case where the WE is a microelectrode, having at least one dimension typically smaller than 100 micrometers. In this case, the currents passed at the WE are small, and therefore a two-electrode cell can be used with a RE, but without the need for a CE.

A "probe" refers to a sensor that contains multiple electrodes. A probe can include, for example, a working electrode, a counter-electrode and a reference electrode (either a conventional reference electrode or a pseudo reference electrode). A probe can include, for example, a working electrode, a counter electrode and an analyte-insensitive electrode (an IWE and PRE).

A "sensor" is an electrode or collection of electrodes that generate a signal in response to the presence of an analyte.

A "surface" of an electrode refers to the functional surface, i.e., that portion of the surface that is in contact with the analyte sample and serves an electrical or electrochemical purpose. It would not, for example, include an insulating WE housing through which no current or voltage passes. The surface of a WE is the portion of the electrode surface in contact with the sample that detects current or electrical potential relative to the RE. The surface of a CE refers to the portion in contact with the sample that serves to deliver or accept current to or from the WE.

A "working electrode" or "WE" is the electrode at which the electrochemical process for detecting the analyte of interest occurs. In a sensor, the working electrode may be sensitive to one or more analyte(s) in the test sample, or it may be chemically modified with analyte sensitive species/materials. The electrochemical response of the working electrode is measured after some perturbation to the system under study has been applied. For example, the perturbation may be the application of a potential difference to the WE that induces electron transfer to occur, and the resulting current at the WE is then recorded as a function of the applied potential (voltammetric mode). This example of mode of operation is illustrative and not exhaustive, as many other modes are known in the art. The WEs of the invention contain an ASM that can undergo a reversible electrochemical redox reaction dependent upon the concentration of analyte (hydrogen ions for a pH meter; other analytes for other analyte sensing devices) in a sample solution and an applied electrical potential. For example, where there is a high concentration of hydrogen ions present in a sample solution, the redox reaction occurs at a lower potential. Conversely, where there is a low concentration of hydrogen ions present in a sample solution, the redox reaction occurs at a higher potential. The relationship between these characteristic potentials and the sample solution pH is a function of the chemical identity of the ASM. An algorithm converts electrical potential to pH value to provide a means of determining the pH of an unknown sample.

With the above definitions in mind, the reader can better appreciate the various aspects and embodiments of the invention described below.

Section 2. Voltammetric Sensor, Instrument with Transmitter Functionality

In some embodiments, the present invention provides a voltammetric sensor for measuring pH comprising a probe, signal processing algorithm, and circuitry that enable display or transmission of measurement results. In some embodiments these components are integrated into a self-contained, optionally hand-held instrument, an illustrative embodiment of which is shown in FIGS. 1 through 3C. In some embodiments, the instrument features a custom connector to facilitate attachment, and replacement of, a removable cartridge that houses the WE, RE, and CE of the voltammetric sensor to a head unit that houses the electronic circuitry, display, and button switches that control various functions of the instrument. The custom connector establishes secure mechanical and electrical connection between the cartridge and head unit.

In other embodiments the voltammetric sensor functions as a transmitter in the context of process control. Some embodiments of this system (which, in some embodiments, is referred to as the SenovaLink™ system (Senova Systems, Inc.)) in accordance with the present invention comprise various components, including but not limited to, sensing elements, firmware and electronics to conduct voltammetric measurements and convert the results into an electrical signal for transmission via cabling or wirelessly to a mobile or remote computing device, and application software for analysis, control, display, and optional further communication with control systems. An illustrative arrangement of these components and their relationship to the analyte sample is shown in block diagram form in FIG. 4. These various components are described in further detail below.

Three primary sensing elements provide the basic function of the voltammetric electrode: the Working Electrode (WE), Reference Electrode (RE) or AIE, and the Counter Electrode (CE). The operating principles and constituents of these electrodes have been described herein and suitable alternative embodiments are described in the patent applications incorporated herein by reference. Optionally, in some embodiments a temperature sensing element (e.g. a thermistor or thermocouple) is included in the vicinity of the other sensing elements to provide information for temperature compensation of the pH information.

The voltammetry electronics provided by the present invention are, in some embodiments, a combination of firmware and specifically designed hardware for driving various sensor elements, capturing the electrochemical response, perform data smoothing and peak picking functions, and converting results into pH readings in accordance with potential-vs-pH calibration information.

The communications interface of these sensor embodiments of the present invention may comprise analog and digital processing circuitry, such as that described above, that produce signals suited for transmission to other digital devices through wired or wireless means. For some embodiments, connecting the electrode system with a mobile or remote computing device requires that they share a common communications interface. Therefore, in some embodiments the transmitting system is equipped with hardware controllers and communications protocols compatible with those on the mobile or remote computing device or other receiving system. Common hardware interfaces are exemplified by USB (Universal Serial Bus), or proprietary connectors exemplified by those used by Apple Computer Co. for its iPhone, iPad, and other devices. Wireless communications protocols and interfaces are exemplified by wireless USB, Bluetooth, ANT+, and other network topologies and communication methods.

Suitable computing devices for use in conjunction with electrode systems described herein include mobile phones, tablet computers, and other portable or stationary computing devices including process controllers. These devices offer processing power, programmability, analysis, display, control, and communication capabilities that complement those of the voltammetric sensor or hand-held instruments derived therefrom, and significantly beyond the functionalities of conventional pH meters. Mobile phones and tablets are increasingly relied upon as a portal of personal and task-specific information. As general-purpose communication and computation platforms, they are configurable to accommodate various levels of complexity and user requirements. Thus mobile or remote computing devices can be versatile replacements for conventional pH meters. A mobile or remote computing device typically comprises the following major functional components: a transceiver for two-way data communication with the SenovaLink pH electrode system; a microcontroller or microprocessor with ancillary analog-digital converters for further processing, if needed, of incoming signal stream; and display and input devices, including touch screen or keyboard. Further, some embodiments of the present invention utilize an Application-Specific Software Program for facilitating communication between a mobile or remote computing device and a SenovaLink™ electrode systems described herein.

For example, in some embodiments an application program is provided comprising an algorithm for optional signal averaging, noise filtering, data comparison, transformation, recording and display for use with an electrode system of the invention. In some embodiments, an application program is provided comprising a user interface for specifying operating conditions, monitoring and diagnosis of the electrode system. As the capabilities of mobile computing devices improve, their functionalities approach have become comparable to those of personal computers such as laptops, desktops, and workstations. The voltammetric sensor functioning as a transmitter is designed to be compatible with any of these computing devices functioning as a receiver and functional extension of the voltammetric sensor.

Figure 4:
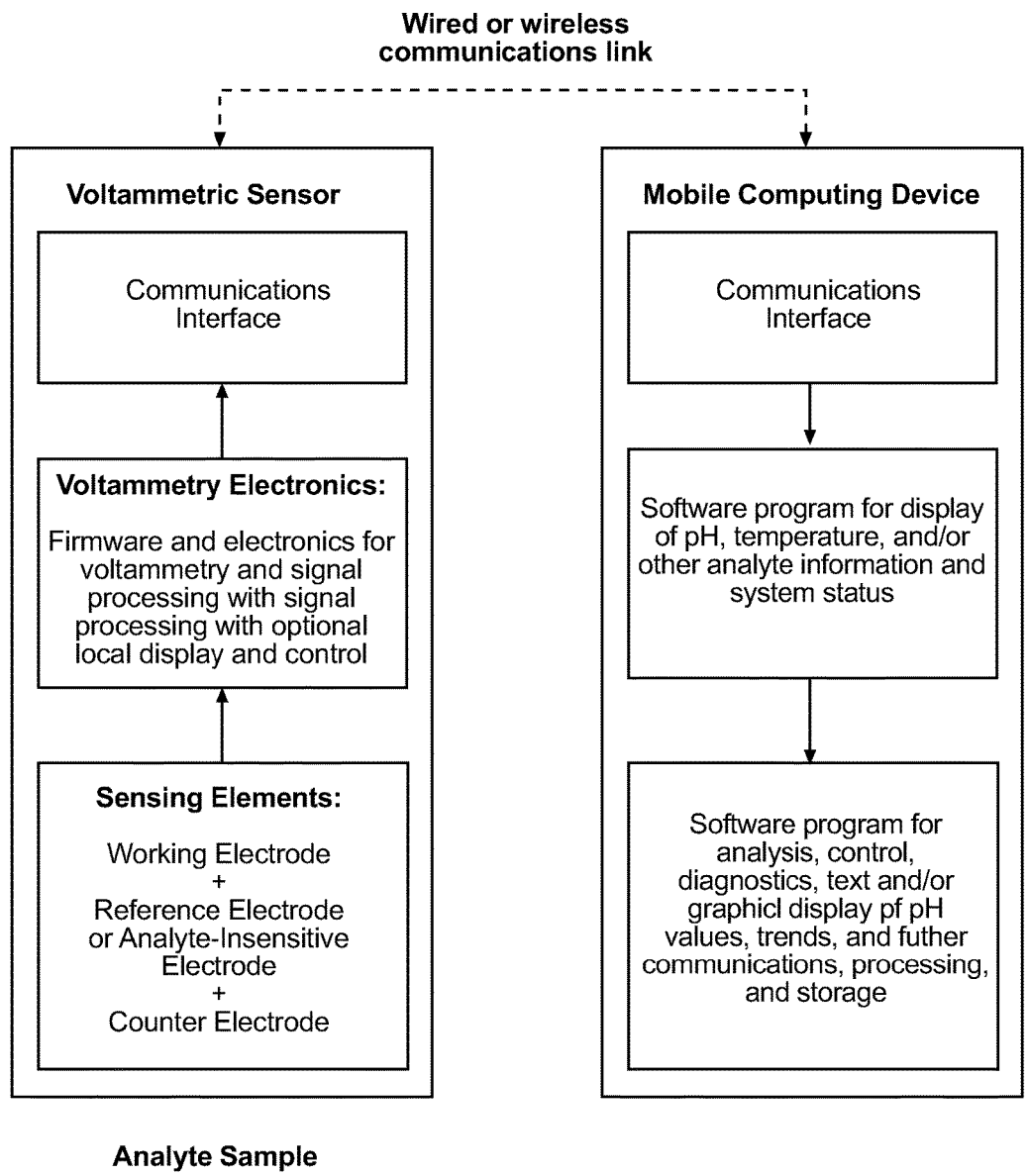
FIG. 4 provides a block diagram of a voltammetric sensor of the invention linked to a mobile (or remote) computer or computing device in accordance with a representative embodiment of the present invention.

With reference to FIG. 4, a representative embodiment of a wired communications link is shown which comprises a USB/VCP (Universal Serial Bus/Virtual Communications Port) connection using suitable cabling. Other embodiments of the wireless communication link comprise a Bluetooth radio frequency communications subsystem.

Figure 5:
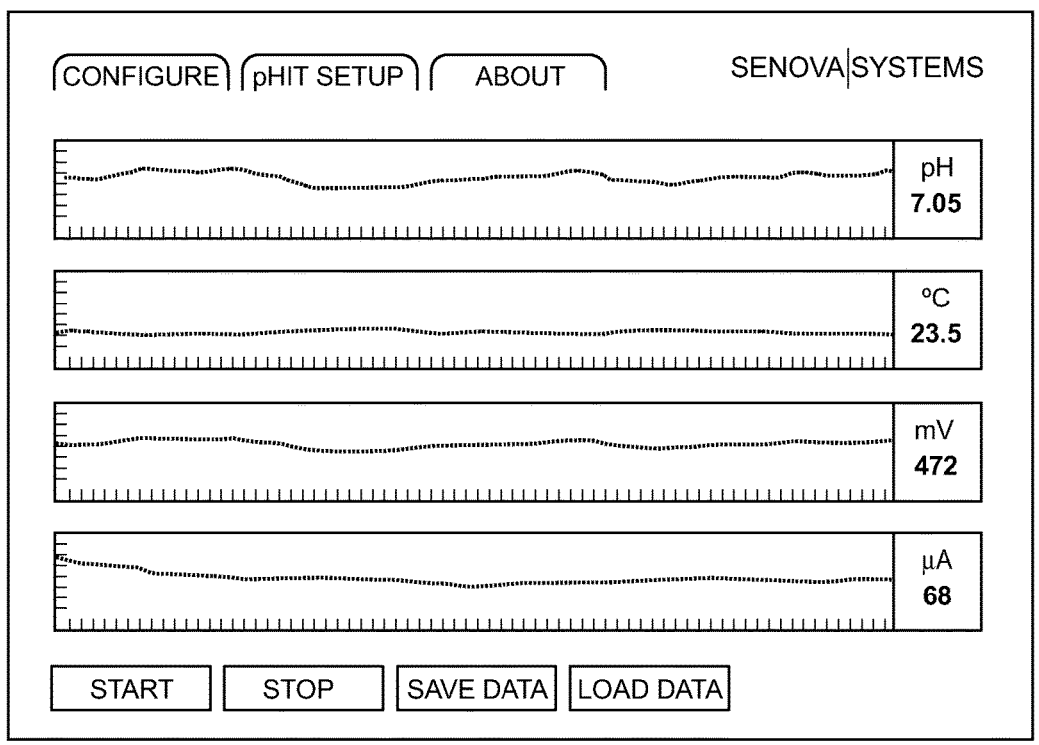
FIG. 5 shows a representative display of voltammetric sensor output, including pH, temperature, current peak position, and peak current as functions of time in accordance with a representative embodiment of the present invention.

In some embodiments, the SenovaLink™ system provides a software program referred to as pHit Reports™ (Senova Systems, Inc.) operating on a laptop or desktop computer. pHit Reports™ hosts a standard graphical user interface and input devices that displays real-time measured values of pH, temperature, current peak potential, and signal strength as functions of time, as shown in FIG. 5. Variations of this graphical user interface can be deployed in mobile phones or tablets displaying selected informational elements. Additional optional features of pHit Reports™ include auto-scaling to keep the captured data displayed within each parametric window; review functions such as cursor control, overlay of multiple data sets, conversion of data to CSV (comma-separated value) files, and storage of captured data in removable memory devices or to industry-standard SQL databases, and other functions.

In other embodiments, SenovaLink™ provides remote control of the operation of the voltammetric sensor from the pHit Reports™ graphical user interface (Senova Systems, Inc., Sunnyvale, Calif.), for example initiating and terminating sequential pH measurements. Other features of the SenovaLink™ system provide firmware loading via the USB interface, data buffering, and automatic disconnect/reconnect logic to minimize data loss during data communication.

Section 3. Voltammetric Sensor to Replace Glass Electrode

In some embodiments of the invention, a voltammetric electrode is provided for use in conjunction with conventional pH meters as a universal replacement of the glass probe. This is accomplished by integrating the functional components of a voltammetric electrode with an emulator, which may be referred to herein as a "universal potentiometry emulator", that converts the electronic signal output representing the measured pH value into a corresponding potential that a conventional pH meter can accept, process, and display.

Figure 6A:
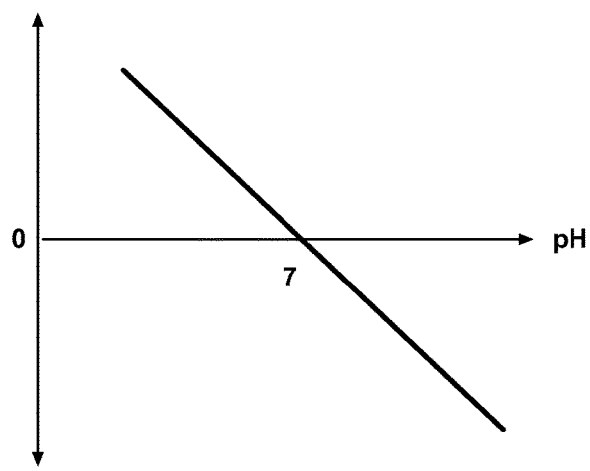
FIG. 6(a) shows the relationship between measured potential and pH for a conventional glass pH electrode.

A conventional pH meter operates by potentiometry, where the potential between a glass pH-sensing electrode and a reference electrode is measured. This potential is a function of the pH of the solution as given by the Nernst equation ($E=E_0+2.3RT/nF*\log[H_3O^+]=E_0+2.3\ RT/nF*pH$, where E is the measured potential, $E_0$ is a constant, R is the gas constant, T is the temperature in degrees Kelvin, n is the ionic charge, and F is the Faraday constant). At 25° C., a pH 7 solution is defined to have a potential E of zero, and the potential varies by 59 mV/pH, also referred to as the slope. This relationship is depicted in FIG. 6(a).

Figure 6B:
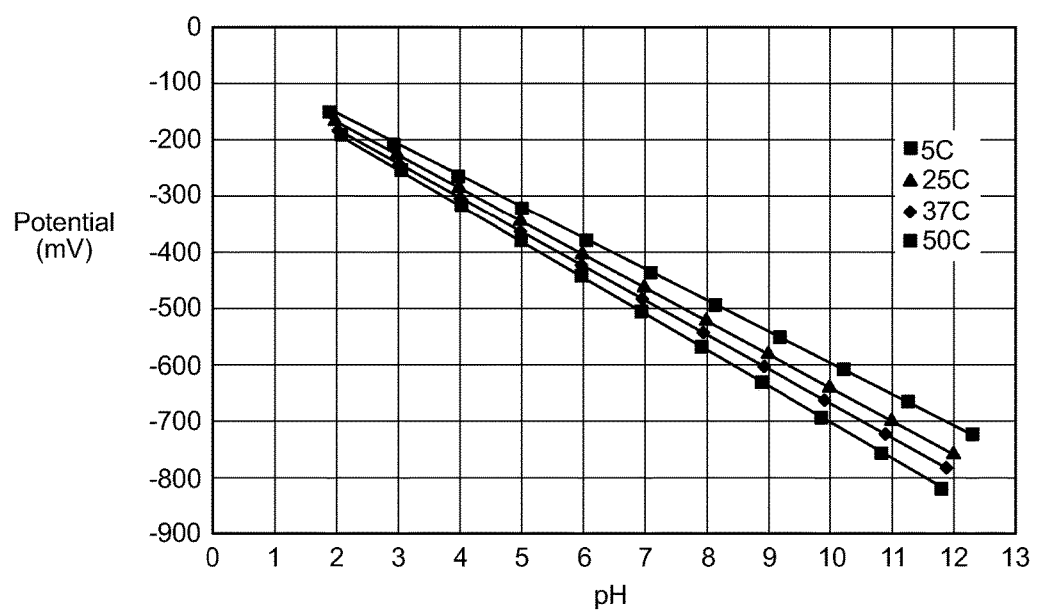
FIG. 6(b) shows the relationship between working electrode potential and pH and temperature for a voltammetric sensor in accordance with a representative embodiment of the present invention.

In the voltammetric sensor of the present invention, a linear relationship also exists between measured potential and pH that varies with temperature. This relationship is dependent upon the identity of the ASM, and the reference electrode system. FIG. 6(b) shows this relationship for a typical embodiment of the invention, measured using standard pH buffer solutions at known temperatures.

Figure 7:
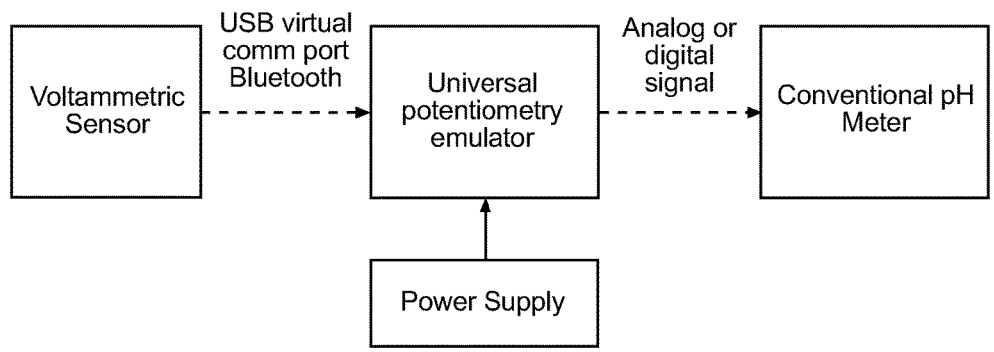
FIG. 7 depicts a universal potentiometry emulator in accordance with a representative embodiment of the present invention.

In operation, the voltammetric sensor sends a commend and temperature-compensated pH information to the universal potentiometry emulator. The emulator then translates the signal and remaps it such that pH 7 corresponds to 0 mV and other pH values follows the 59 mV/pH slope (i.e. pH 8=+59 mV, and pH 6=−59 mV). The voltage thus generated is sent to the differential input of a conventional pH meter in analog or digital form depending on the design of the conventional pH meter. FIG. 7 illustrates this process which is referred to as the SenovaOmni™ system (Senova Systems, Inc.).

For some embodiments, the emulator comprises a microprocessor programmed to remap the signal from the voltammetric sensor to an output conforming to the Nernst equation. In other embodiments the emulator further comprises a digital-to-analog converter. In most embodiments a temperature-sensing element is incorporated in the voltammetric sensor. Temperature information from this sensor is used to compute the potential and pH output in the manner depicted in FIG. 6(b). Thus the converted signal mimics the behavior of a glass electrode, but requires no further temperature compensation by the conventional pH meter. In some embodiments the universal potentiometry emulator is an accessory connected to the conventional pH meter by cabling and BNC connectors, or wirelessly with components that enable that function. Connection to the voltammetric sensor wirelessly is facilitated by the embedded wireless subsystems already present, or via suitable cabling such as USB. In some embodiments the functions of the universal potentiometry emulator is incorporated in the electronic circuitry of the voltammetric sensor, optionally in the same housing and powered by the same source. Some electrodes provided by the invention are plug-compatible replacements for glass pH electrodes in widespread use. In some embodiments the emulator is built into a conventional pH meter to render it suitable for use in conjunction with the voltammetric sensor of the present invention. Such integration facilitates specific implementation of communication protocols and optimized electronic, mechanical, and industrial design.

Section 4. Improved Reference Electrodes

The voltammetric sensor of the invention includes a reference electrode (RE), which can be a conventional RE, a pseudo-RE, an analyte insensitive electrode (AIE), or an improved version of the foregoing provided by the present invention.

A number of conventional reference electrodes suitable for use in a probe of the present invention are known in the art. See, for example, Bard and Faulkner, "Electrochemical Methods: Fundamentals and Applications" (Wiley 2001), incorporated herein by reference.

In some embodiments of the invention, the conventional reference electrode is a chloridized silver wire surrounded by an electrolytic solution. In other embodiments, the conventional RE is only a chloridized silver wire. In other embodiments, the conventional RE is an iodide/tri-iodide system as described in U.S. Pat. No. 4,495,050, incorporated herein by reference. In other embodiments, the conventional RE is a standard calomel electrode.

In some instances, a "pseudo-reference electrode" (PRE) (sometimes referred to as "quasi-reference electrode") is used, particularly for non-aqueous solutions, in an analyte sensor of the invention instead of a conventional RE. An illustrative but non-limiting example of a PRE is a silver wire, commonly used in non-aqueous electrochemistry. Another example of a PRE is a platinum wire. Other PREs may be used according to the particular application. PREs are also used in sensors of the invention that comprise a WE and an AIE, as the AIE comprises a PRE and IWE, as discussed more extensively below.

In some embodiments, the surface area of the conventional RE exposed to the analyte sample is selected so as to minimize or eliminate events that adversely affect analyte-dependent signal quality.

Thus, the present invention also provides a variety of embodiments in which a solid-state working electrode (WE) featuring a redox-active analyte-sensitive material is operated in conjunction with a conventional RE or PRE in the same pH metering system. This hybrid approach combines the robustness inherent in solid-state devices and the accepted reference standard upon which much of electrochemistry science is based.

Thus, one of ordinary skill in the art will appreciate the unique hybrid configuration of various embodiments of the present invention. In particular, one of ordinary skill in the art will appreciate the present combination of a solid-state WE with a conventional RE, typically with a CE as well. This hybrid configuration provides a pH probe assembly having the reliability of a conventional RE without the known drawbacks of traditional glass working electrodes. Thus, the present invention provides new and useful combinations of electrodes that overcome the limitations of traditional pH (or other analyte) probes and metering systems.

In some embodiments, the invention provides an analyte insensitive electrode (AIE) that is used in lieu of a conventional RE in a sensor of the invention. The AIE is capable of generating a substantially analyte insensitive signal in response to the application of an electrical stimulus applied to the sample being analyzed in the course of making voltammetric or amperometric measurements of analyte concentration in the sample. The AIE provides a predictable signal useful as an internal standard (in other words, a standard internal to the system) with which an analyte-sensitive signal may be continuously compared, and therefore permit greater accuracy and reproducibility in determining analyte concentration. Thus, in some embodiments of the present invention, an AIE is used in the electrochemical analyte sensing device to generate a substantially analyte-insensitive electrical response when an electrical stimulus is applied to an analyte sample in the course of making voltammetric and/or amperometric measurements of analyte concentration.

The teachings of the current invention regarding different WE chemistries (see below) are also applicable to certain embodiments of the AIE. Specifically, an AIE can feature the same pH- (or other analyte-) responsive surface chemistry as the WE and, due to its specially-formulated constant chemical environment and the PRE it contains, used to replace the conventional RE (such as Ag/AgCl/KCl). See PCT Pat. Pub. No. 2010/104962, incorporated herein by reference.

Conventional REs operate by establishing a stable, well-characterized electrode potential. The stability of this electrode potential derives from a redox system with constant activities of each participant of the redox reaction. Stable electrode potentials are obtainable using electrodes with covalently-attached ASM (or AIM) matrix material as the sensing surface. These electrodes generate highly reproducible electrode potentials in a constant chemical environment such as that provided by a buffered material, such as a buffer solution. Thus, some embodiments of an AIE of the invention contain a redox-active matrix material of the invention, optionally attached to a substrate, and a PRE in a buffer solution contained within an enclosed volume. This enclosed volume is, in turn, in fluid and electrical communication through a liquid barrier such as a porous frit with the analyte solution. In operation, this AIE is co-located with the WE and the CE, and each electrode is in direct contact with the analyte solution. Regardless of whether a redox active material is characterized as an ASM or AIM, it can be made analyte-insensitive by sequestration in a properly formulated ionic medium, as contained in an AIE.

In operation, the AIE exhibits an electrode potential dependent largely on the nature of the redox active material and the nature of the constant chemical environment in which it is sequestered, i.e., in a properly formulated ionic medium. As described in PCT Pub. No. 2010/104961, a variety of suitable ionic media exist; in some embodiments, the suitable ionic media is simply a buffer (which may be a solid or semi-solid) or buffer solution. For example, as illustrated in the examples below, a suitable ionic media includes a commercially available pH 7 buffer as received from the vendor (VWR part #BDH5056-20L), an example of a buffer solution; or a liquid pH 7 buffer with hydroxyethyl cellulose added as a viscosity enhancer (Sigma Aldrich part #434973-250G), an example of a semi-solid buffer; or a semi-solid pH7 buffer with KCl (Sigma Aldrich part #P3911-2.5KG) added as a means for increasing ionic strength and preserving the chloridized silver PRE. When the suitable ionic media is a liquid, an appropriate liquid barrier is also employed so that convective mixing between the analyte sample and the liquid ionic media is reduced to insignificant levels on the time scale of interest. Appropriate liquid barriers include, without limitation, membranes and frits, as discussed below and illustrated in the examples herein. Any ingress of the analyte sample across the liquid barrier will only exert a minimal effect on the constant chemical environment provided by the liquid ionic media because of the inherent ability of the buffer solution in the liquid ionic media to mitigate pH shifts due to composition changes. The result is an exceptionally stable electrode potential compared with conventional REs such as Ag/AgCl/KCl, in which the KCl solution has no significant buffering capacity. This fundamental advantage of the AIE over conventional REs, coupled with the stability derived from covalently-attached or physically entrapped ASM (or AIM) matrix material, results in unexpectedly superior performance of this new class of pH probes containing such AIEs.

The AIE and the WE function similarly in that both are redox-active electrodes. In some embodiments of a sensor of the invention, the redox-active material and matrix containing it (the IWE) in the AIE and the WE are identical or substantially similar. In other embodiments of the sensor, the AIE and the WE have different chemical compositions, i.e., they differ in the redox-active compound employed or in the matrix employed, or both. The latter embodiments offer additional degrees of freedom and greatly expand the different types of pH (and other analyte) sensing systems of the invention, in that the AIE and the WE may be individually tailored to deliver the most beneficial combination of physical and performance attributes. For example, the WE can be based on a chemical composition designed to offer the highest accuracy over a broad pH range, whereas an alternate WE can be based on a chemical composition designed to withstand aggressive chemical environments such as strong acids or alkalis. In either case, the AIE can be based on a chemical composition exhibiting the highest precision in the presence of a neutral buffer to offer the longest life expectancy for the AIE. The chemistry options described in the present invention, including various linking chemistries, enable control of WE properties to meet these diverse needs.

In various embodiments of the current invention, an AIE in which the constant chemical environment is in the form of a semi-solid or a solid is employed.

Thus, in some embodiments, the constant chemical environment of the AIE is provided by a solid or semi-solid material (the "reference material") that provides buffering capacity, electrical conductivity, and ionic permeability. In other embodiments, the reference material is a hydrophilic solid with sufficient ionic content to serve as a conduit of hydrogen ions in the analyte solution, and a conductor of electrical current between the CE and the AIE. The reference material is in direct contact with the analyte on one side, and with the functional surface of the redox-active material and with the PRE on the other side. In some embodiments, the reference material is selectively permeable to hydrogen ions but substantially impermeable to other entities in the analyte solution, so that the redox-active material within the AIE will not be exposed to a changing chemical environment during use. Suitable reference materials include crosslinked zwitterionic polymers with compositions that mimic those of liquid buffer solutions; for example, a combination of strongly basic and weakly acidic functionality, or a strongly acidic and weakly basic functionality. Upon hydration, such polymers would maintain its inherent pH value even as small amounts of acid or base comes into contact with, or diffuses into, the polymer structure.

In some embodiments of the current invention, a gelling agent is added to a conventional buffer solution to convert it into a solid buffer material. An example of such a gelling agent is agarose, which is soluble in hot water but undergoes gelation upon cooling. This behavior enables a buffer solution containing agarose to assume a congealed rubbery state at ambient operating temperatures, providing a non-fluidic constant chemical environment largely determined by the buffer solution.

In various other embodiments, the reference materials can be prepared by formulating ionic monomers to yield a target pH in the finished polymer, effecting polymerization, and placing the resultant polymer in contact with the IWE to form an AIE. In cases where a crosslinked polymer is deployed, polymerization can be conducted in-situ, i.e., in direct contact with the IWE. The following are non-limiting examples of suitable illustrative precursors to a variety of polymeric reference materials for use in AIEs of this invention:

(1) Crosslinked acrylamide-based hydrophilic polymers comprising: (I) N,N-dimethyl acrylamide; (II) N,N-methylenebisacrylamide as crosslinker; (III) 2-acrylamido-2-methylpropane sulfonic acid as the strong acid component; and (IV) N-[3-(Dimethylamino)propyl]-methacrylamide as the weak base component. In the resultant polymer, the characteristic pH is largely determined by the stoichiometric ratio of III and IV:

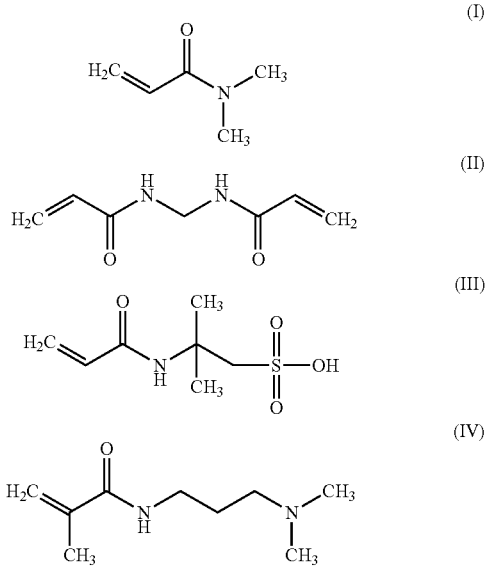

(2) Silane derivative of 4-(2-hydroxyethyl)-1-piperazine ethanesulfonic acid (HEPES).

HEPES is an organic buffering agent containing a sulfonic acid group and tertiary amino groups in the same molecule. Thus the stoichiometric ratio of strong acid-to-weak base groups is constant at unity:

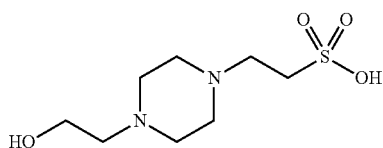 [SMILES: O=S(=O)(O)CCN1CCN(CCO)CC1]

This attribute is carried over to the derivative SEN-01-14b, shown below, which is a silane derivative of HEPES capable of reacting with other sol-gel precursors such as TEOS. This results in a solid zwitterionic polymer with buffering properties. By conducting the sol-gel conversion on the surface of the IWE, a constant chemical environment is formed in direct contact with the RAM sensing surface.

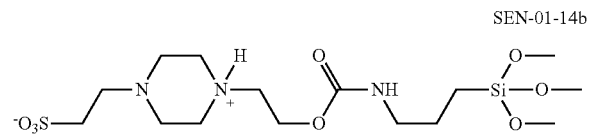

In some embodiments, regardless of whether the constant chemical environment is a liquid, semi-solid, or solid, a barrier is used at the interface between the constant chemical environment and the analyte to substantially prevent ingress of the analyte into (e.g. by mixing with, or dissolution in) the constant chemical environment. This barrier may be in the form of a liquid or a solid.

If a liquid is used as the barrier, it should be immiscible with a liquid constant chemical environment, or have minimal solubility in a semi-solid or solid reference material employed as the constant chemical environment of the AIE. Such a barrier may be in the form of an ionic liquid or room-temperature ionic liquid, in which case a porous matrix can be used to hold the liquid by capillarity and to assume the physical form factor of the porous matrix, such as a porous frit or a microporous membrane.

This liquid barrier may also be in the form of an ionomer, which is a synthetic polymer with ionic properties. One type of ionomer barrier provided by the invention comprises, consists of, or consists essentially of a sulfonated tetrafluoroethylene-based fluoropolymer-copolymer, including but not limited to Nafion (marketed by DuPont). This material is permeable to protons but not anions, is hydrophilic, and exhibits excellent chemical resistance and biocompatibility. Certain other proton-conducting membranes and composites exhibit similar attributes and are suitable alternatives for the present invention. (See, for example, Mustarelli et al., Advanced Materials, 20 (2008) 1339-1343; Viswanathan et al., Bulletin of the Catalysis Society of India, 6 (2007) 50-66). With such liquid barriers, the AIE overcomes problems associated with maintaining wet reference systems, may be stored dry until use, and may be kept dry between exposures to analyte solutions, i.e., has wet-dry reversibility. In some embodiments, a sheet of Nafion membrane is used to seal one end of a tube. Inside the tube is placed a buffer solution as the constant chemical environment. When the tube is placed in an analyte solution, the Nafion prevents the two solutions from mixing. Other forms of constant chemical environment described herein, including liquid, semi-solid, or solid, can be used instead of the buffer solution. In all cases the ionomer membrane also serves as a barrier against penetration of substances in the analyte other than protons into the constant chemical environment that might affect its composition.

Nafion is supplied commercially in the form of solid films, or as precursor solutions that can be heated and solidified. Solid Nafion films are available in a limited range of thicknesses. It is well known in the art that Nafion solutions or other ionomer precursor solutions can be incorporated into various porous supports to provide form factors suitable for their intended use. (See, for example, Proton Conductors, P. Colomban, ed., Cambridge University Press, 1992). For the present invention, a composite membrane is formed by using a microporous membrane to immobilize the Nafion solution, and then heat treating to form a continuous Nafion phase in the porous structure. This approach combines the dimensional stability of the microporous membrane substrate with the chemical and electrochemical properties of Nafion. Suitable microporous membranes are exemplified by polysulfone, polyethersulfone, polyvinylidenefluoride, in pore sizes commonly available for microfiltration. The composite membrane can be conveniently fabricated by methods known to the artisan, including heat sealing and ultrasonic welding, typically prior to immobilizing the Nafion solution or precursors to other ionomers. Furthermore, as illustrated in Example 5 below, a reference electrode comprising a Nafion type liquid barrier is capable of dramatically reducing the rate of water transport across that barrier while remaining hydrated, even without constant contact with an external preservation solution (such as buffer or KCl solution required by conventional pH electrodes with frit-type liquid junctions). As a result, the change in composition due to loss of reference solution is greatly reduced. At the same time, Nafion type ionomers are permeable to protons but virtually impermeable to anions by charge exclusion, and are excellent barrier to medium to large molecules. These attributes allow electrodes of the current invention to resist severe degradation of function when stored in the dry state, and obviates the need for wet preservation between routine use in analyte solutions.

In other embodiments, microporous materials can also be used as substrates for preparing composite membranes of Nafion or other ionomers. These include but are not limited to ceramic or glass frits, especially where the reference material is a solution or semi-solid, or ceramic or glass membranes where the reference material is a solid. The use of solid porous substrates such as frits or wafers prepared from polymers or inorganic materials impart mechanical rigidity in electrode constructs where additional robustness is needed.

In other embodiments of this invention, a voltammetric electrode comprising a WE, a CE, and a wet-dry reversible AIE reference is constructed entirely in solid-state. In some embodiments, a first conductive substrate is used as foundation for the WE, upon which a matrix material containing the ASM is deposited to form the analyte-sensitive surface. A second conductive substrate is used as foundation for the AIE. On this substrate are deposited layers of material in the following order to obtain the analyte-insensitive surface: 1) A matrix material comprising a RAM; 2) a solid or semi-solid reference material serving as a constant chemical environment; 3) a PRE comprising Ag/AgCl, platinum, or other suitable material embedded in the reference material, and 4) an analyte barrier comprising Nafion or other suitable ionomer. Independent electrical connections are made with the first conductive substrate bearing the WE, the second conductive substrate bearing the RAM, and the PRE. A functional voltammetric electrode is formed by co-locating the WE, AIE, together with a CE which is also independently electrically connected, typically in the form of a cluster of sensors, and performing square-wave voltammetry in accordance with methods described in this invention. In some embodiments, the conductive substrate comprises a rigid material that is inherently conductive (such as metals, carbon, or conductive polymers) or rendered conductive by means of coatings (such as conductive inks or pastes) or chemical treatments (such as chemical vapor deposition or corona discharge). In other embodiments, the conductive substrate is a flexible material such as a polymer film (for example and without limitation, polyethyleneterephthalate, polyimide, polyetherimide, and polyvinylidenefluoride), a fabric (for example nonwoven polyester), a wire or conduit, or elements and combinations thereof, with compositions described above. The advantages of rigid or flexible solid-state electrodes enabled by the current invention are numerous and compelling for many intended uses and specialized applications beyond the reach of conventional glass electrodes and pH measurement systems on which they are based.

In other embodiments of this invention, the barrier properties of a membrane with selective permeability may be beneficially incorporated as a surface coating on the WE to shield it from interfering species in the analyte. Such membranes include, but are not limited to, Nafion membrane constructs.

Section 5. Improved Voltammetric Working Electrodes

In other embodiments, the invention provides improved voltammetric working electrodes. These electrodes comprise a RAM (which may be an ASM or AIM) covalently attached to or entrapped within a matrix material prepared from a synthetic polymer. The resulting matrix material exhibits both the intrinsic properties of the polymer, which functions as a framework to secure the RAM while offering spatial dispersion for contact between analyte and the ASM (when the RAM is an ASM), bonding with a conductive substrate, and the analyte-responsive (e.g. pH-responsive) functionality required in a WE or the appropriate functionality required for an AIE. Synthetic polymer attributes of interest as matrix materials include, but are not limited to, good film-forming properties, compatibility with conductive substrates, adjustable mechanical properties such as rigidity, strength, ability to be shaped into different form factors, and a wide range of properties attainable by blending, copolymerization, crosslinking, grafting, and physical or chemical modifications at the bulk or surface levels. These attributes permit the design and fabrication of electrodes in sizes, form factors, and performance to meet different requirements. A general approach in some methods of the invention is to use a RAM with suitable functional groups reactive to complementary functional groups in the matrix polymer. Those skilled in the art will recognize, upon contemplation of this disclosure, that the RAM, when covalently attached to the polymer, can be situated along the backbone of the matrix polymer and/or on branches or side-chains of the matrix polymer, and that by introducing the RAM as functionalized tethers, crosslinkers, or chain-extenders, a myriad of different matrices of the invention can be prepared.

In some embodiments, a RAM is incorporated into inherently conductive polymers to derive sensors in which the electrochemical signals generated by the RAM can be efficiently captured and transmitted directly to electronic processing circuits via the conductive polymer. In this aspect, the resulting electrode does not have a traditional conductive substrate, which can be advantageous. For example, in the case of a WE used in a pH meter, eliminating the interface between the pH-sensitive matrix material and a separate conductive substrate resolves several problems associated with the physical, chemical, and electronic compatibility of dissimilar materials. The use of polymers, including conductive polymers, helps reduce the complexity and improve design flexibility and manufacturability of electrodes assuming various form factors (including size, shape, flexibility, mechanical design, disposability, and the like), and so provides means to fabricate the flexible sensors and miniaturized sensors of the invention.

In some embodiments, a WE is prepared using matrix material of the invention based on AQ covalently bound to poly(vinyl alcohol), or PVA. The finished structure comprises an alkanyl backbone and an ether-linked side chain to which the AQ moiety is tethered. PVA exhibits excellent resistance to chemical attack, as does the ether linkage connecting the AQ. PVA is also an excellent film-forming polymer. Furthermore, PVA can be crosslinked by chemical and thermal means, further enhancing the dimensional and environmental stability of the finished structure. These are all desirable properties in a pH (or other analyte) sensor expected to encounter a wide range of operating conditions.

In other embodiments, polymers exhibiting good physical, chemical, and mechanical attributes that can be functionalized to attach ASM (or AIM) moieties are generally suitable alternatives to PVA, and can be preferred alternatives to PVA for specific applications and/or fabrication methods. Such polymers include, but are not limited to, derivatives of polysulfone, polyethersulfone, polyamides, polysulfonamides, polyimides, polyesters, vinyl polymers, polyphenylene sulfide, polysaccharides, cellulose, derivatives thereof, copolymers thereof, blends thereof, and composites thereof. ASM (or AIM) attachment methods include, but are not limited to, reaction with functionalized ASMs (AIMs), grafting of polymers already containing ASMs (or AIMs) as tethers, interpenetrating networks of multiple polymer or oligomer components in which at least one of the components comprise covalently-attached ASM (or AIM) moieties.

In other embodiments, a suitably derivatized RAM is incorporated as monomer or co-monomer in the preparation of a polymer. This approach is exemplified by the reaction of a bifunctional anthraquinone derivative with a diisocyanate:

For those embodiments in which the ASM (or AIM) is entrapped within but not covalently attached to the matrix, the ASM (or AIM) can be incorporated into the matrix by physical or mechanical means. Such means include, for example, mixing or compounding solid forms of the ASM (or AIM) and the preformed matrix material, typically with the addition of a binder or followed by melting and solidification. Alternatively, the ASM (or AIM) can be added as a solution, colloidal dispersion, or suspension into a solution of the matrix precursor. Conversion of the precursor into a solid matrix then immobilizes the ASM (or AIM) homogeneously at the molecular level, e.g. as discrete aggregates or as distinct physical domains.

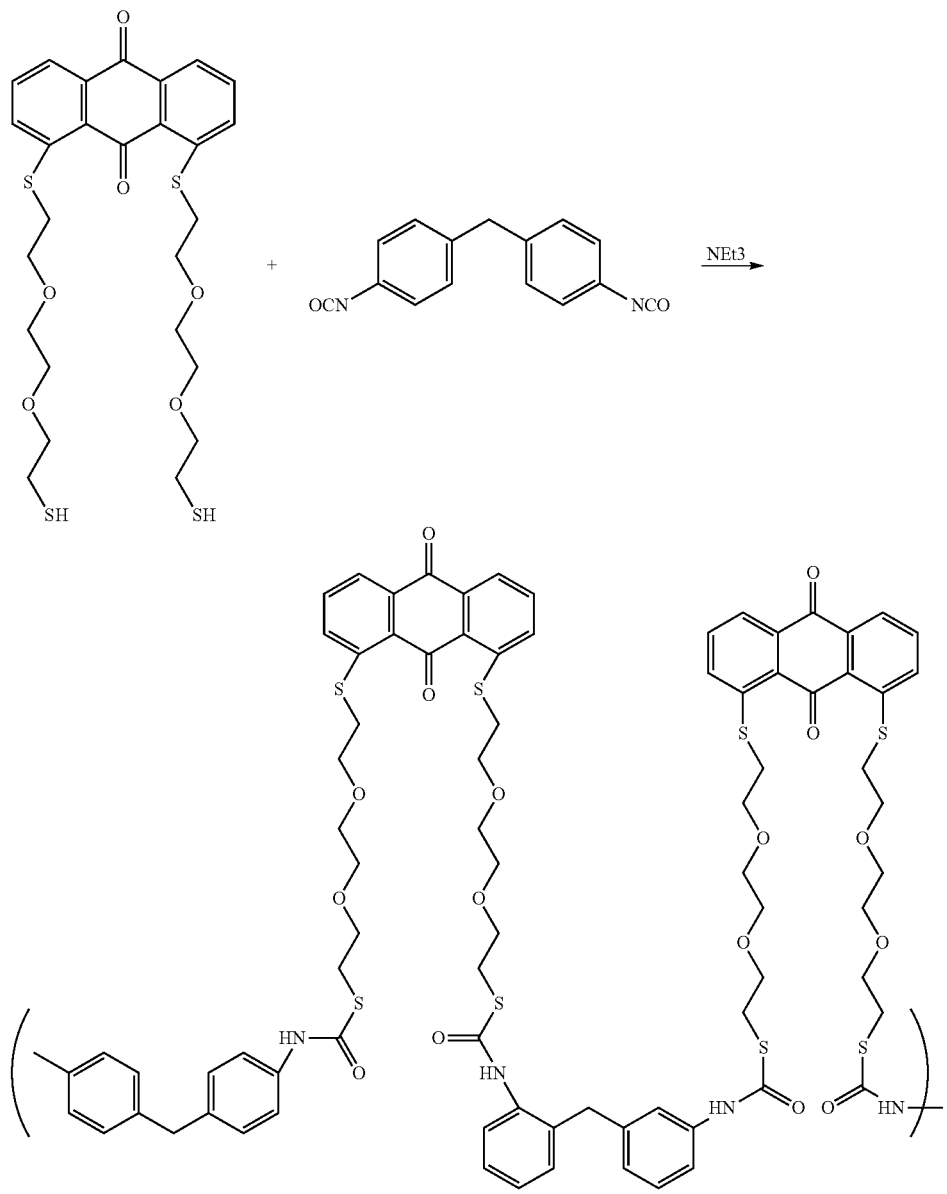

The ordinary skilled artisan will recognize that various combinations of reactants can be used to prepare a range of polymers with desirable properties within the scope of this invention.

In some embodiments, the matrix material of the current invention comprises an ASM covalently attached to a mechanically and chemically stable matrix material. In some embodiments, the matrix material of the current invention comprises an ASM non-covalently entrapped within a mechanically and chemically stable matrix material. In some embodiments, the matrix material is attached to a substrate surface. In other embodiments, the matrix material alone serves as the electrode (i.e., there is no separate substrate). In many embodiments, the matrix material is in the form of a surface coating (composed of a sol-gel or other polymeric material) on a conductive substrate, which together form a WE (or IWE of an AIE). In the case of a WE, the matrix material in this embodiment functions to attach the ASM to a solid structure (the conductive substrate), offer unhindered access of the analyte sample to the ASM, and provide efficient electrical connection between the ASM and the conductive substrate. In some embodiments, the matrix material contains more than one ASM, which differ from one another in the potential at which they sense the analyte. The advantage of this multiple ASM system is the greater degree of precision and accuracy associated with multiple data points being taken in the same measurement. Another advantage of this multiple ASM system is its ability to maintain accurate sensing of the analyte concentration even if certain components of the test sample interfere with the normal response of one of the ASMs.

In some embodiments, the present invention provides a matrix material (a sol-gel or polymeric material) that contains both an ASM and an AIM. A theoretical advantage of this system is that a separate reference electrode may be unnecessary in the system, because the signal derived from the AIM is used for the point of reference (see PCT Pub. No. 2005/085825). As with the WE described immediately above, in some embodiments of this electrode, the matrix material contains one or more ASMs as well as one or more AIMs.

Further, in some embodiments, the present invention provides a matrix material (for example, a sol-gel or other polymeric material) that contains one or more AIMs and/or one or more ASMs in a suitable electrical environment such that the resulting electrode functions as an IWE of an AIE.

Suitable ASM materials may include, for example and without limitation: pH sensitive ASMs: anthraquinone (AQ), phenanthrenequinone (PAQ), N,N'-diphenyl-p-phenylenediamine (DPPD), anthracene, naphthaquinone, para-benzoquinone, diazo-containing compounds, porphyrins, nicotinamides, including NADH, NAD$^+$ and N-methylnicotinamide, quinone thiol, monoquaternized N-alkyl-4,4'-bipyridinium, RuO, and Ni(OH)$_2$, ferrocene carboxylate, and derivatives of those compounds; CO-sensitive ASMs: ferrocenyl ferraazetine disulfide; iron porphyrins; alkaline metal cation sensitive ASMs: 1,1'-(1,4,10,13-tetraoxa-7,1-diazacyclooctadecane-7,16-diyl dimethyl), ferrocenyl thiol, other ferrocene derivatives containing covalently attached cryptands, and certain metal complexes with Fe$^{2+}$/Fe3$^+$, Co2$^+$/Co3$^+$, Cu$^+$/Cu2$^+$. Suitable ASMs are described, for example, in Hammond et al., J. Chem. Soc. Perkin. Trans. 707 (1983); Medina et al., J. Chem. Soc. Chem. Commun. 290 (1991); Shu and Wrighton, J. Phys. Chem. 92, 5221 (1988), and PCT Pub. No. 2010/111531, each of which is incorporated herein by reference. Illustrative examples include the above ferrocenyl ferraazetine and ferrocenyl cryptands, in which an ordinarily chemically insensitive redox center (ferrocene) is covalently linked to a chemical recognition site in such a way as to make its redox potential chemically sensitive. Also suitable are molecules or polymers in which the sensor and reference functionalities are covalently linked, such as 1-hydro-1'-(6(pyrrol-1-yl)hexyl-4,4'-bipyridinium bis (hexafluorophosphate), as described by Shu and Wrighton, J. Phys. Chem. 92, 5221 (1988), incorporated herein by reference. Additionally, a wide range of substituted anthraquinones has been developed for the dyestuff industry. Many compounds from that legacy exhibit redox active properties suitable for use in the present invention. For example and without limitation are mono-, di-, or poly-hydroxyl substituted AQ; mono-, di-, or poly-amino substituted AQ, ethyleneglycol or polyethyleneglycol-modified AQ, and the like. The artisan will recognize the myriad choices available that, with appropriate screening and further functionalization, can yield additional ASMs suitable for use in the invention.

In some embodiments, the WE comprises two or more ASMs sensitive to the same analyte species, which are selected so as to provide a more sensitive measurement than is provided by a single ASM while minimizing the possibility of introducing additional overlapping peaks which must be resolved to determine analyte concentration. In some examples of this embodiment, the WE comprises both phenanthrenequinone (PAQ) and anthraquinone (AQ). In other embodiments, the WE comprises two or more ASMs sensitive to the same analyte species selected to ensure that not all of them are equally susceptible to potentially interfering species, especially redox couples, that may be present in a test sample. Other compounds such as benzalkonium chloride, a quaternary ammonium chloride, may adversely interfere with ASMs such as AQ and PAQ, for example. An ASM less susceptible to such interference may be for example a derivative with one or more functional groups that sterically or ionically hinder the approach of an interfering species. In any event, an ASM can be covalently attached to or non-covalently entrapped within a matrix material, as described herein, that provides such hindrance. In other embodiments, the WE may further comprise an AIM as an internal standard, as described above. Still further, in some embodiments the WE comprises two or more ASMs, each ASM being selected for sensitivity to a different analyte species.

In one aspect, the present invention provides a matrix material and corresponding electrodes, probes, pH meters and other analyte sensing devices in which an ASM (and/or AIM) is covalently attached to or non-covalently entrapped within a matrix material prepared from a silane-modified ASM (and/or AIM) precursor and alkoxysilanes using a sol-gel process. Sol-gel processing is a technique often used in materials science that transforms a colloidal solution (sol) to an integrated network matrix material (gel) (see *Sol Gel Science: The Physics and Chemistry of Sol-Gel Processing*, C. J. Brinker and G. W. Scherer, Academic Press, 1990, incorporated herein by reference). The resulting matrix material typically exhibits certain characteristics of ceramic and glass, as well as the pH-responsive functionality (in the case where the redox active material is an ASM selected for use in a WE to be used in a pH sensor) required in a pH sensor. Preparation of these matrices can involve the following illustrative compounds, compositions, and methods of the invention below.

In a first step, a silane precursor with the general structure of Formula (I), below, or salts, hydrates and/or solvates thereof, is synthesized:

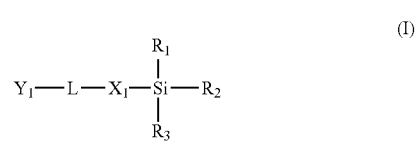

wherein: at least two and typically all three $R_1$, $R_2$ and $R_3$ are independently alkoxy or aryloxy, and if only two are alkoxy or aryloxy the third may be alkyl or aryl; $X_1$ is —O— or a chemical bond; L is a linker; $Y_1$ is a linking group. Suitable linking groups includes but are not limited to —$CO_2H$, halogen, —OH, —$NHR_4$, —$SO_2H$, —$R_5CO$, —$P(O)(OR_6)(OH)$, —$N_3$ or —CN, wherein $R_4$, $R_5$ and $R_6$ are independently hydrogen, alkyl, or aryl. The composition of the silane-modified ASM precursor, including the nature of the -L- linkage, determines the electochemical response, longevity, and chemical resistance of the resulting electrode and sensor containing the electrode.

Generally, $X_1$ can be any kind of chemical functionality that can form a covalent bond with silicon, and many such functionalities are known to those of skill in the art (see, for example, Sol-Gel Science for Ceramic Materials, S. K. Young, in Material Matters, Vol. 1, No. 3, pp 8-10, Sigma-Aldrich, 2006, incorporated herein by reference). In some embodiments, $X_1$ is simply a chemical bond. Connected to $X_1$ is a linking moiety of the formula $Y_1$-L, where L is a linker and $Y_1$ is a linking group. The nature of linker L and linking group $Y_1$ can, as will be appreciated by those of skill in the art upon contemplation of this disclosure, vary extensively. The linker L may be hydrophilic or hydrophobic, long or short, rigid, semi-rigid or flexible.

A wide variety of linkers L comprised of stable bonds suitable for spacing linking groups such as $Y_1$ from the silicon group are known in the art, and include, by way of example and not limitation, alkyl, aryl, arylalkyl, polycyclic aryls, esters, ethers, polymeric ethers and the like. Thus, linker L may include single, double, triple or aromatic carbon-carbon bonds, etc. Further, alternative embodiments of L include branched structures that influence the spatial configuration of the ASM, including orientation, distance from the sol gel network, the flexibility of the linkage, and/or electron transfer efficiency. In some embodiments, L is a conjugated system or multiple conjugated systems.

Choosing a suitable linker will be within the capabilities of those having skill in the art upon contemplation of this disclosure. For example, where a rigid linker is desired, L can be a rigid polyunsaturated alkyl or an aryl, biaryl, and the like. Where a flexible linker is desired, L can be a flexible saturated alkanyl. Hydrophilic linkers can be, for example, polyols (polyalcohols), such as poly(vinyl alcohol) and its derivatives, or polyethers, such as polyalkyleneglycols. Hydrophobic linkers can be, for example, alkyls or aryls.

Alternative embodiments of L include alkyl, aryl, allyl, ether, esters alkoxyl, amide, sulfonamide, and other linkages, including heterocyclic, linear, cyclic, acyclic, or mixed conjugated linkages. The linking group $Y_1$ should be capable of mediating formation of a covalent bond with a complementary reactive functionality of an ASM to provide an isolated silane-modified ASM precursor of the invention. Accordingly, linking group $Y_1$ can be any reactive functional group known to be suitable for such purposes by those of skill in the art upon contemplation of this disclosure. $Y_1$ can be for example, a photochemically activated group, an electrochemically activated group, a free radical donor, a free radical acceptor, a nucleophilic group or an electrophilic group. However, those of skill in the art will recognize that a variety of functional groups that are typically unreactive under certain reaction conditions can be activated to become reactive. Groups that can be activated to become reactive include, e.g., alcohols, carboxylic acids, including salts thereof.

Thus, in some embodiments, $Y_1$ is —$CO_2H$, halogen, —OH, —$NHR_4$, —$SO_2H$, —$R_5CO$, —$P(O)(OR_6)(OH)$, —$N_3$, —CN, aldehyde, thiol, alkene, or alkyne.

Some embodiments of $Y_1$-L include for example, compounds where L is —$(CH_2)_n$—, n is an integer between 1 and 8, $Y_1$ is $CO_2H$, halogen, —OH, —$NHR_4$, —$SO_2H$, —$R_5CO$, —$P(O)(OR_6)(OH)$, —$N_3$ or —CN. In some embodiments, $Y_1$ is —$CO_2H$, halogen, —OH, —$NHR_4$ or —$N_3$. In some embodiments, L is —$(C_2H_2)_n$— where n is an integer between 1 and 24.

In some embodiments, $R_1$, $R_2$ and $R_3$ are independently alkoxy, L is —$(CH_2)_n$, $X_1$ is a chemical bond, $Y_1$ is —$CO_2H$, halogen, —OH, —$NHR_4$ or —$N_3$ and n is an integer between 2 and 6. In other embodiments, the silane precursor has the structure of Formula (II):

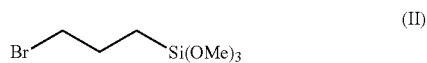

(II)

In still other embodiments, the silane precursor has the structure of Formula (III):

(III)

A wide variety of conventional methods may be used to prepare the silane precursors above and well within the ambit of the skilled artisan. For example, nucleophilic displacement of a silyl chloride (i.e., Cl—$SiR_1R_2R_3$) with $Y_1$L-M or $Y_1$-L-O-M, where M is a metal can provide the silane precursors above.

In a second step, used in those embodiments in which the RAM is covalently attached to the matrix material, an ASM (or AIM) group is covalently attached to the silane precursor to provide an ASM (or AIM) silane precursor of the invention of Formula (IV) depicted below (ASM1 is also represented herein as $ASM_1$):

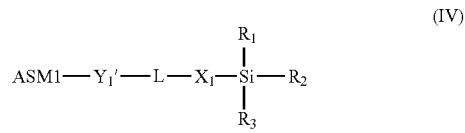

(IV)

wherein: at least two and typically all three $R_1$, $R_2$ and $R_3$ are independently alkoxy or aryloxy, and if only two are alkoxy or aryloxy the third may be alkyl or aryl; $X_1$ is —O— or a chemical bond; L is a linker; $Y_1$' is a linking group. Suitable linking groups include, but are not limited to —$CO_2NR_4$—, —O—, —$NR_4CO$—, —$SO_2$—, —$R_5CO$—, —$P(O)(OR_6)$ O—, —$CO_2$—, —$O_2C$—, —$NR_4O_2$—, —$O_2CNR_4$, —N=N—, or a chemical bond, wherein $R_4$, $R_5$ and $R_6$ are independently hydrogen, alkyl, or aryl. ASK in Formula IV is an analyte sensitive material (or analyte insensitive material, or a derivative of either). In general, ASK is considered a derivative of an ASM (or AIM), because, in the structure of Formula IV, it differs from the corresponding ASM (or AIM) by loss of a hydrogen atom as necessitated by formation of a covalent bond to either $Y_1$ or (when $Y_1$ is a chemical bond) L. In some embodiments, $R_1$, $R_2$ and $R_3$ are independently alkoxy; L is —$(CH_2)_n$, $X_1$ is a chemical bond; $Y_1$' is —$CO_2NH$, or —O—, or —$NHR_4$; and n is an integer between 2 and 6.

In some embodiments, ASK is selected from the group consisting of Formulas V, VI, VII or VIII:

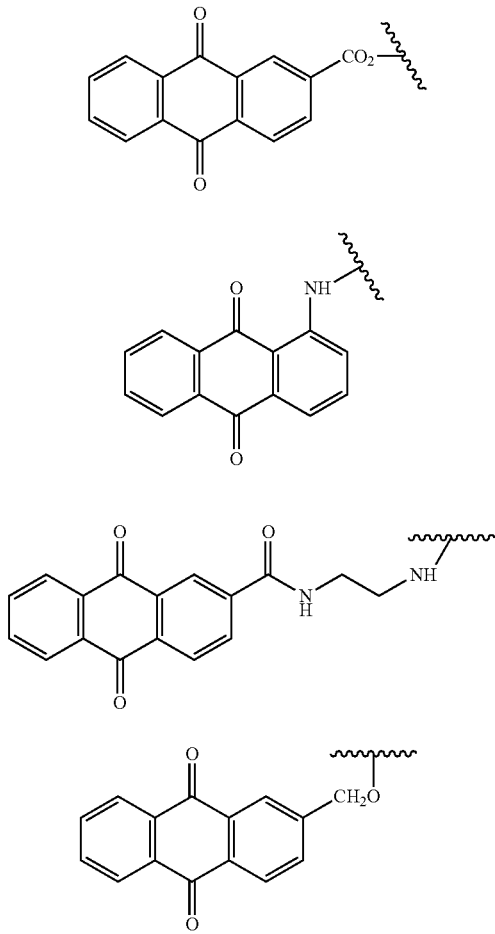

In other embodiments, ASM₁ is derived from an ASM selected from a group consisting of Formulas IX, X, XI, XII, XIII, XIV, XV and XVI:

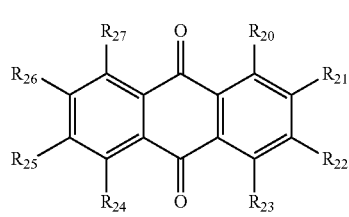

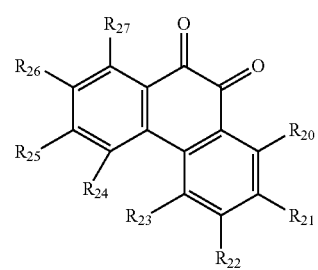

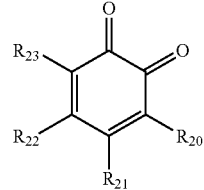

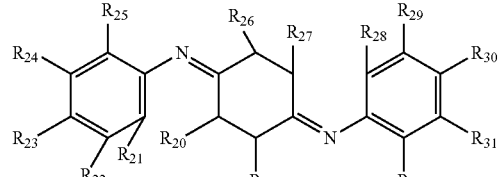

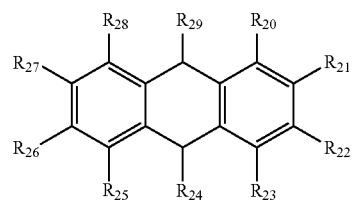

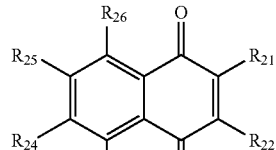

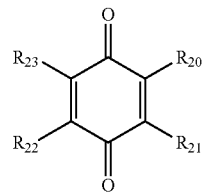

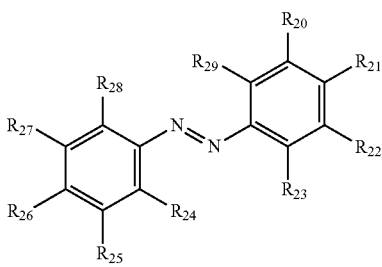

wherein $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$ and $R_{33}$ are independently hydrogen, —CO₂H, halogen, —OH, —NHR₄, —SO₂H, —R₅CO, —P(O)(OR₆)(OH), —N₃, —CN, alkyl, aryl or alkoxy with the proviso that least one substituent is —CO₂H, halogen, —OH, —NHR₄, —SO₂H, —R₅CO, —P(O)(OR₆)(OH), N₃ or —CN.

In some embodiments, the ASM silane precursor of the invention has the structure of Formula XVII:

(XVII)

For clarity, the CON in the preceding structure is a carbonyl group linked to a nitrogen (the N thus has a hydrogen attached to it that is not shown in the structure). In other embodiments, the ASM silane precursor of the invention has the structure of Formula XVIII:

(XVIII)

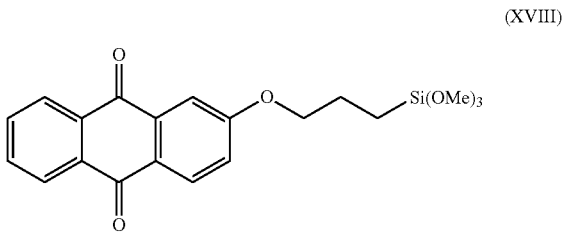

Still, in other embodiments, the ASM silane precursor of the invention has the structure of Formula XIX:

(XIX)

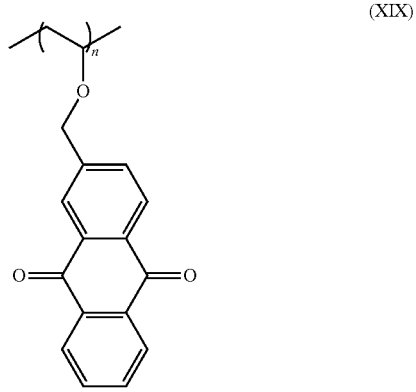

Generally, the ASM silane precursor of Formula (IV) can be assembled from the silane precursor of Formula (I) and an appropriately functionalized ASM using conventional methods of organic synthesis. These include, for example, ester, amide, and sulfonamide condensations, alkylations, 1-3 dipolar cycloadditions, and carbene, nitrene and free radical additions between complementarily functionalized compounds of Formula (I) and ASMs. Thus, the invention also provides new compounds that are complementarily functionalized ASMs suitable for use in such synthetic methods.

In a third step, used in those embodiments in which the RAM is covalently attached to the matrix material, a sol comprising the ASM (or AIM) precursor, a polyalkyl orthosilicate or similar multifunctional silane, solvents, an acid catalyst, and optionally other additives is prepared. At this point, the silane groups in the ASM (or AIM) precursor and the polyalkyl orthosilicate or similar multifunctional silane hydrolyze and undergo crosslinking, converting sol to gel.

The resultant sol-gel is heterogeneous to some degree, comprising both liquid and solid regions whose morphologies can range from discrete particles to continuous structures of varying porosities. In the process, the ASM (or AIM) is also incorporated into the crosslinked network to form a matrix of the invention, as shown in the following reaction scheme:

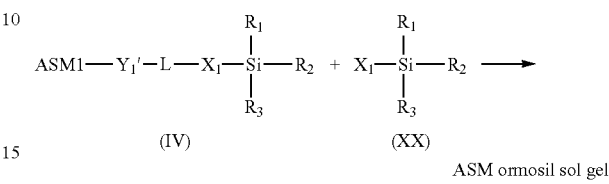

ASM ormosil sol gel

The term "ormosil" stands for "organically modified silica/silicate."

In the scheme above, at least two and typically all three $R_1$, $R_2$ and $R_3$ are independently alkoxy or aryloxy, and if only two are alkoxy or aryloxy, the third may be alkyl or aryl. Each of these moieties is independently selectable. Thus, if $R_1$ in Formula IV is methoxy, $R_1$ in Formula XX can be aryloxy or another alkoxy, and if $R_2$ and $R_3$ in Formula XX are alkoxy or aryloxy, then $R_1$ in Formula XX can be alkyl or aryl, even if $R_1$ in Formula IV is methoxy. Typically, in compounds of Formula I, Formula IV, and Formula XX, at least two and often all three of $R_1$, $R_2$ and $R_3$ are independently methoxy or ethoxy. Following formation of the sol-gel, a coating of this material, which is still in liquid form, is applied onto a prepared conductive substrate. Finally, solvents are removed under controlled thermal treatment conditions (especially temperature, pressure, and time) which results in a stable structure with ASM covalently bonded to, and dispersed throughout, the matrix material which is substantially in contact with the conductive substrate, thereby forming an electrode of the invention. Thus, the matrix is the analyte (e.g. pH)-sensitive surface of a working electrode of the invention, or is itself formed into the electrode (in those embodiments where no conductive substrate is employed, but the matrix material itself is conductive). If an AIM is used as ASM1, then the matrix serves as the active surface of the IWE of the AIE, or is itself formed into the IWE (in those embodiments where no conductive substrate is employed, but the matrix material itself is conductive).

Those skilled in the art will recognize that these methods may be used to create sensors containing one or more ASMs, one or more AIMs, and combinations of ASM(s) and/or AIM(s). Such combinations can provide additional response signals that vary with analyte identity and concentration, and/or reference signals substantially unchanged with analyte identity and concentration. Such combinations are therefore within the scope of the present invention.

In some embodiments, the sol-gel matrix material comprises a single ASM (or a single AIM). For example, some embodiments of single ASM pH WEs comprise a sol-gel matrix material in which the ASM is selected from the group of compounds consisting of 2-carboxy AQ, 2-N—BOCethylene diamine AQ, 5,12-naphthacene quinone, 1-acetyl amido AQ, 2-carboxamido AQ, and 3-carboxamido PAQ. In other embodiments, a single ASM WE comprises a sol-gel matrix material in which the ASM is 2-(beta-naphthol) methylanthraquinone. As stated above, other suitable ASMs may be identified for use with or without derivatization for the purpose of this invention.

In other embodiments, the sol-gel matrix material of the present invention comprises at least two or more ASM (or ASM and AIM) compounds. Thus, some embodiments of the present invention comprise a sol-gel matrix material having at least one ASM and optionally comprise one or more additional ASMs and/or an AIM(s). Both the ASMs and AIMs include redox-active materials exhibiting reversible redox activity with well-defined cyclic voltammetry methods.

Some embodiments of the present invention may further include a sol-gel matrix material incorporating an AIM component having a redox potential that is substantially insensitive to the chemical medium to which the sensor is introduced. Such AIMs may include, for example and without limitation AIMs selected from the group comprising ferrocene, n-butyl ferrocene, $K_4Fe(CN)_6$, polyvinyl ferrocene, nickel hexacyanoferrate, ferrocene polymers and co-polymers, including ferrocene styrene copolymer and ferrocene styrene cross-linked copolymer, nickel cyclam, and others. Further, non-limiting examples include ferrocenyl thiol, polyvinyl-ferrocene, viologen, polyviologen and polythiophene. Other embodiments include AIMs comprising ordinarily chemically sensitive materials which are chemically isolated, yet in electrical contact with the chemical medium or analyte sample.

In other embodiments, an AIM, such as, for example, a substituted ferrocene such as that depicted below as Formula XXI, is covalently attached to a matrix material prepared from a silane-modified AIM precursor and alkoxysilanes using a sol-gel process.

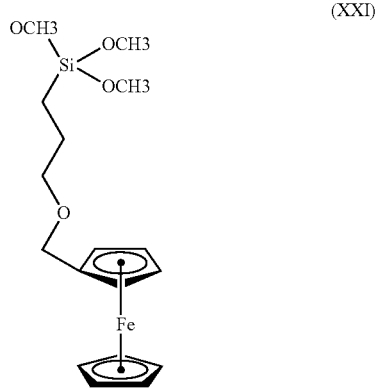

(XXI)

This AIM precursor and similar AIM precursors featuring alternative linking groups are compounds of the invention that can be used as the basis of an AIM covalently attached to a matrix material based on the sol-gel chemistry-based methods of the invention. The AIM precursor can be used in admixture with an ASM precursor to form an electrode that produces an analyte-sensitive signal and an analyte-insensitive signal. Alternatively the AIM precursor can be used to form a discrete structure (an AIE) generating a single, analyte-insensitive signal, which can be used in conjunction with an analyte-sensitive signal produced by a co-located WE.

In other aspects of this invention, a combination of a single ASM, a plurality of ASMs, an AIM, and/or a plurality of AIMs, are covalently attached to a matrix material prepared from alkoxysilanes and a silane-modified ASM (or AIM) precursor using a sol-gel process, or covalently attached to a matrix material prepared from an optionally crosslinked polymer, or non-covalently entrapped within a matrix material prepared from a matrix material prepared from alkoxysilanes, polymers, or cross-linked polymers.

In some embodiments, the concentration of ASM on the WE (or AIM on the WE or the IWE of the AIE) is increased by applying multiple layers of ASM (or AIM)-containing sol-gel matrix material or polymeric matrix material to the WE (or AIE) substrate. In accordance with the present invention, the ordinarily skilled artisan can control the amount of ASM (or AIM) contained in the matrix material placed onto the substrate, thereby permitting the manufacture of WEs (or AIEs) and probes containing them having a size and shape appropriate to a given application to achieve additional benefits of the invention.

In some embodiments, the WE comprises ASM present in a sufficient amount to result in a pH-dependent signal of between 1 and 500 microamperes. In some embodiments, the size and shape of the WE are chosen so as to minimize deleterious electrochemical effects among the WE, RE and CE (or WE, AIE, and CE) while maintaining WE performance sufficient to allow a user to distinguish the analyte-dependent signal over background noise while maintaining signal quality.

The WEs (and AIEs) of the present invention may be configured so as to be removable from the probe, allowing them to be easily interchanged or replaced according to the required design and functionality. As discussed above, the WEs of the invention can be configured and programmed to replace a traditional glass probe in a traditional pH meter and/or to generate a signal that is transmitted by electrical wiring, or via electromagnetic means not requiring wires, to a readout device.

Some embodiments of the present invention further provide improved analyte sensors having one or more WEs, each comprising one or more ASMs entrapped within a sol-gel or other polymeric matrix material and disposed on a substrate and in electrical connection with that substrate.

In some aspects, the WE comprises an AQ derivative as an ASM. In other aspects, the present invention provides a WE that comprises phenanthrenequinone (PAQ) or a derivative thereof as an ASM. Further, in other aspects the present invention provides a WE that comprises ortho-benzoquinone (OQ) or a derivative thereof as an ASM. Still further, in other aspects, the present invention provides a WE that comprises N,N-diphenyl para-phenylene diamine (DPPD) or a derivative thereof as an ASM.

In some aspects, the present invention provides an electrode that comprises anthracene (AC) or a derivative thereof as an ASM. In other aspects, the present invention provides an electrode that comprises naphthoquinone (NQ) or a derivative thereof as an ASM. Further, in other aspects the present invention comprises provides an electrode that comprises para-benzoquinone (PQ) or a derivative thereof as an ASM.

Those of skill in the art will appreciate, in view of this disclosure that, in general, many of the teachings herein that concern ASMs are equally applicable to AIMs.

A variety of substrate materials are suitable for use in the WEs and AIEs of the present invention in which a substrate is employed. These suitable substrate materials include but are not limited to carbon, carbon allotropes, and derivatives thereof, various carbon-based materials, transition metals, noble metals such as gold and platinum, conductive metal alloys, various conductive polymers and copolymers and compounds and derivatives thereof, polymer blends and polymer composites, semiconductive materials such as silicon and derivatives thereof, including doped silicon and doped semiconductive materials, mixtures or composites of any of these materials, and additional suitable materials known to those of skill in the art.

In some aspects, the substrate is or comprises carbon. A variety of carbon substrates are suitable for use as substrate material in the electrodes of the present invention, including but not limited to carbon allotropes such as pyrolytic graphite, graphite, amorphous carbon, carbon black, single- or multi-walled carbon nanotubes, graphene, glassy carbon, boron-doped diamond, pyrolyzed photoresist films, and others known in the art. Additionally, all of the above carbon allotropes may be dispersed in powder form in a suitable binder, or formed in-situ on the substrate surface. Such binders include organic or inorganic polymers, and adhesive materials. In some embodiments, the substrate is graphite powder and the binder is epoxy resin. In other embodiments, the substrate is a graphite rod. In other embodiments, the substrate is a carbon fiber composite. In other embodiments, the substrate is a graphite-filled polymer exemplified by, but not limited to, polyphenylene sulfide. In other embodiments, the substrate comprises a surface coating of an ink formulated with one or more carbon allotropes. In other embodiments, the substrate comprises a surface coating of an ink formulated with one or more metals exemplified by silver, gold, and platinum. In other embodiments, the substrate is an ionomer (exemplified by Nafion marketed by DuPont Co.). In other embodiments, the substrate is an ionomer containing a dispersion of carbon allotrope particles, carbon nanotubes, carbon nanowires, graphene, metal, or other compatible agents for enhancing the physical and electronic properties of the matrix including, but not limited to, assisting transmission of electronic signals from the RAM.

Thus, in some embodiments, the substrate comprises a composite material comprising graphite and a binder, such as an epoxy. In some embodiments, the substrate comprises a composite material comprising carbon fibers and one or more binders. In some embodiments, the substrate comprises a conductive polymer such as polyaniline, polypyrrole, or various carbon allotrope-filled polymers, where the polymer components may include, without limitation, polyphenylene sulfide, polyolefins, polyamides, polyimides, polyesters, polysulfone, polyethersulfone, various vinyl polymers, cellulose, poly(amino acids), derivatives thereof, copolymers thereof, blends thereof, and composites thereof. In some embodiments, the substrate comprises materials surface-treated by corona discharge, electron beam, gamma irradiation, plasma, and other forms of irradiation that result in an activated surface by ion or free radical generation. Optionally, such activated surface may be further modified to enable attachment of ASM (or AIM) derivatives or matrix materials containing covalently attached or non-covalently entrapped ASM (or AIM) moieties.

In some aspects of the invention, the surface of the substrate is cleaned or otherwise "prepared" prior to applying the ASM (or AIM) containing sol-gel or polymeric matrix material. Suitable methods for graphite/epoxy substrates and other substrates include but are not limited to sanding and/or polishing the surface of the substrate, which may be formed into a plug, followed by directing a stream of pressurized air or other gas onto the substrate surface, and optionally sonicating in a suitable solvent, to dislodge particulates resulting from sanding or polishing. Alternatively, and optionally, the substrate surface may be cleaned with various solvents, alkalis, and/or acids, followed by thorough removal of such cleaning agents by means well known to the skilled practitioner. These methods, applied selectively to substrates compatible with the treatment conditions and chemicals, serve to remove superficial contamination prior to attachment of the ASM (or AIM)-containing matrix material, thereby improving the security of attachment of the matrix material to the substrate and useful life of the sensor.

A substrate acts as a self-contained entity that serves as a physical and electrical bridging unit between one or more ASMs (or AIMs) within the sol-gel or polymeric matrix material, and an electrical conduit, such as a wire. The physical function of the substrate is to provide a support for the ASM (or AIM) sol-gel or polymeric matrix material such that the electrode may be brought into direct contact with a sample of interest, typically a liquid, safely and conveniently in the form of a probe or a functionally equivalent assembly. The substrate and matrix material thereby allow the ASMs (or AIMs) to interact with the sample of interest. The electrical function of the substrate is to propagate charge carriers such as electrons from the electrical conduit to the ASM (or AIM) to enable a redox reaction. In some embodiments, a substrate material is selected to be chemically inert to the anticipated environments of the sample to be analyzed, and an ability to conduct electrical current with minimal loss.

As discussed above, Virtually all embodiments of the present invention are probes that include a counter electrode (CE). In operation, the CE serves as an electron source or sink, delivering current through the analyte sample to the other electrodes within the pH probe.

Suitable CEs are known in the art. See, for example, Bard and Faulkner, above. To avoid unwanted electrochemical redox processes occurring at the CE that can interfere with the signal measured at the WE, the CE is typically made of a relatively chemically inert material, commonly stainless steel, carbon (e.g., graphite) or platinum.

In some embodiments, as illustrated in the examples below, the CE is a graphite or carbon-based rod. In other embodiments the CE is a carbon-fiber tube. Still further, in some embodiments the CE is another electrically conductive material, as known in the art.

Various references describe the importance of the CE:WE surface area ratio to sensor performance. In various embodiments of the present invention, the surface area of the CE exposed to the analyte sample is selected so as to minimize or eliminate intra-electrode electrochemical effects that adversely affect analyte-dependent signal quality and longevity, as described herein. In some embodiments, the ratio of the surface area of the CE to that of the WE is from about 1:0.5 to about 1:20.

In some embodiments, the CE comprises an electrically conductive carbon-fiber or stainless steel tube having a hollow inner lumen for housing various other components of the pH sensor. The carbon-fiber or stainless steel tube is electrically coupled to a preamplifier module whereby a voltage is applied to the sample solution via the CE. One skilled in the art will appreciate that, in addition to providing electrochemical cell driving potential, the electrically conductive, low-impedance CE serves as an electromagnetic shield to protect components housed within CE, especially the high-impedance RE, from external electromagnetic interference. In some embodiments, a coaxial configuration is implemented whereby an external position of the CE provides electromagnetic shielding to the RE and WE, which electrodes are concentrically or approximately concentrically positioned within the CE. One skilled in the art will further appreciate that the shielding function of the CE is not dependent upon the concentric positioning of the RE and WE. Rather, one skilled in the art will appreciate that the exact positions of the RE and WE may be internally altered relative to the external position of the CE and still receive the shielding protection as discussed above.

The principles and methodologies of the current invention regarding the creation of WEs (and IWEs) embodying certain desirable attributes can be applied to various designs of electrodes, probes, sensor assemblies, analyte measuring devices, meters and systems, and instrumentation. Each of these deployments will benefit from the advantages of electrodes of the current invention over conventional electrode systems, in particular those based on glass probes, and specifically glass pH probes.

Those of skill in the art will appreciate upon contemplation of this disclosure that there are many alternative ways of implementing and realizing the many benefits and advantages afforded by the various aspects and embodiments present invention. Accordingly, the present embodiments are to be considered as illustrative and not restrictive, and the invention is not to be limited to the details given herein, but may be modified within the scope and equivalents of the appended claims. All publications and patents cited herein are incorporated by reference in their entirety. The following examples are provided for illustrative purposes only and do not limit the scope of the invention.

EXAMPLES

Figure 10:
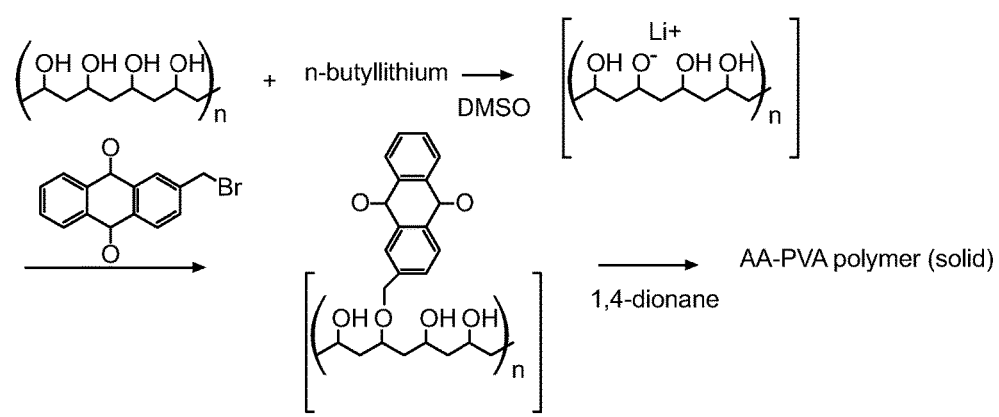
FIG. 10 is a chemical procedure whereby polyvinyl alcohol (PVA) is functionalized with anthraquinone (AQ) in accordance with a representative embodiment of the present invention.

Example 1. Anthraquinone-Poly (Vinyl Alcohol) Conjugate (AQ-PVA) and Working Electrodes Derived Therefrom Polyvinyl alcohol (PVA) was functionalized with AQ using the procedure shown in FIG. 10.

PVA (0.53 g, Alfa Aesar, 86-89% hydrolyzed, low molecular weight) was added to a dry three-neck round bottom flask containing an egg shaped stir bar. The flask was purged with argon and all subsequent steps were performed under argon. Anhydrous DMSO (25 mL, Aldrich) was added through a syringe. The mixture was stirred and heated for 30 minutes at 50° C. to dissolve the PVA. The solution was cooled to room temperature and n-butyllithium (1.0 mL, 1.6M in hexane, Aldrich) was added drop-wise over about 30 seconds using a 1 mL syringe. A gel formed at the top surface was broken up by rapid stirring and the addition of 10 mL additional DMSO. The reaction mixture appeared to be homogeneous after 1 h of continuous stirring. 2-Bromomethylanthraquinone (0.5 g, Aldrich) was added in one portion as a solid and the solution became green-black and opaque. The mixture was stirred for 12 h, becoming a dark, homogeneous solution. The solution was poured into rapidly stirred 1,4 dioxane (350 mL, Aldrich) in a 1000 mL Erlenmeyer flask. Initially, the dioxane solution was brown and homogeneous, but after stirring 3 h the solution lightened to yellow and a brown solid formed.

The brown solid was collected by vacuum filtration using a glass frit (10-20 micron). The solid in the filter was washed with four times with 50 mL portions of 1,4 dioxane until the filtrate was colorless. About 700 mg of dry AQ-PVA polymer was obtained as a brown powder on the filter. The polymer was stored in a capped glass vial at room temperature in the dark.

Figure 11:
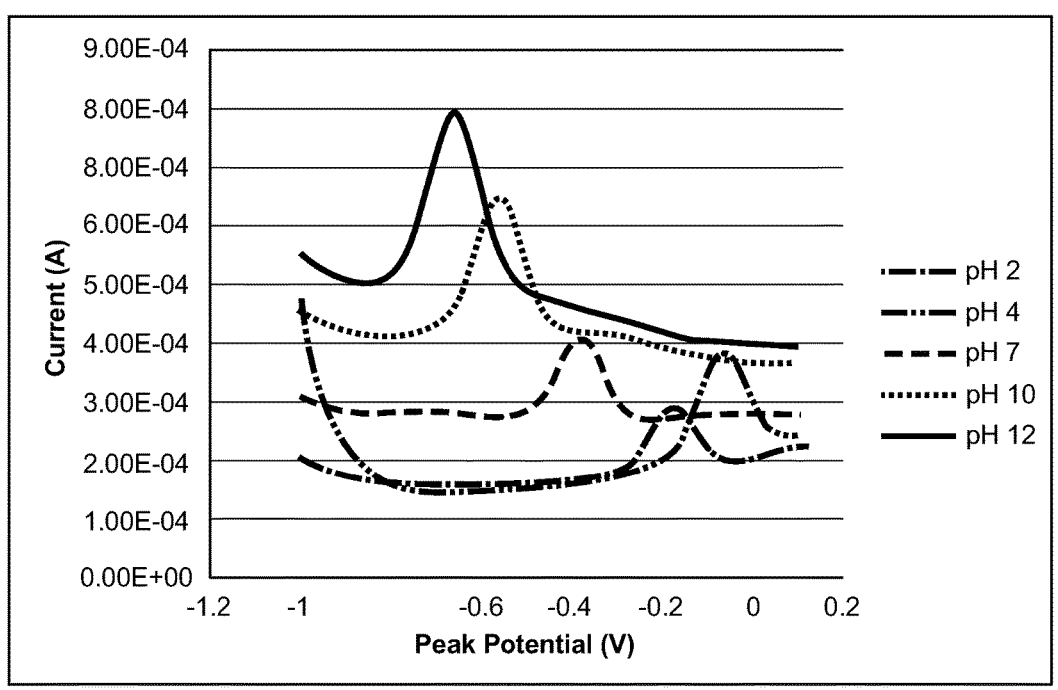
FIG. 11 is a graph displaying the results of an electrode tested using standard square-wave voltammetry in five buffer solutions in accordance with a representative embodiment of the present invention.

AQ-PVA coated carbon fiber electrodes were prepared by dissolving the polymer in dimethylacetamide (50° C., 6 mg/mL final concentration), depositing a 2 microliter aliquot on the cleaned carbon fiber substrate surface and heating the electrodes at 100° C. for 1 h. An electrode was tested using standard square-wave voltammetry in five buffer solutions at pH 2, 4, 7, 10, and 12. Results are shown FIG. 11, where current I (in A) was measured as a function of potential E (in V).

Figure 12:
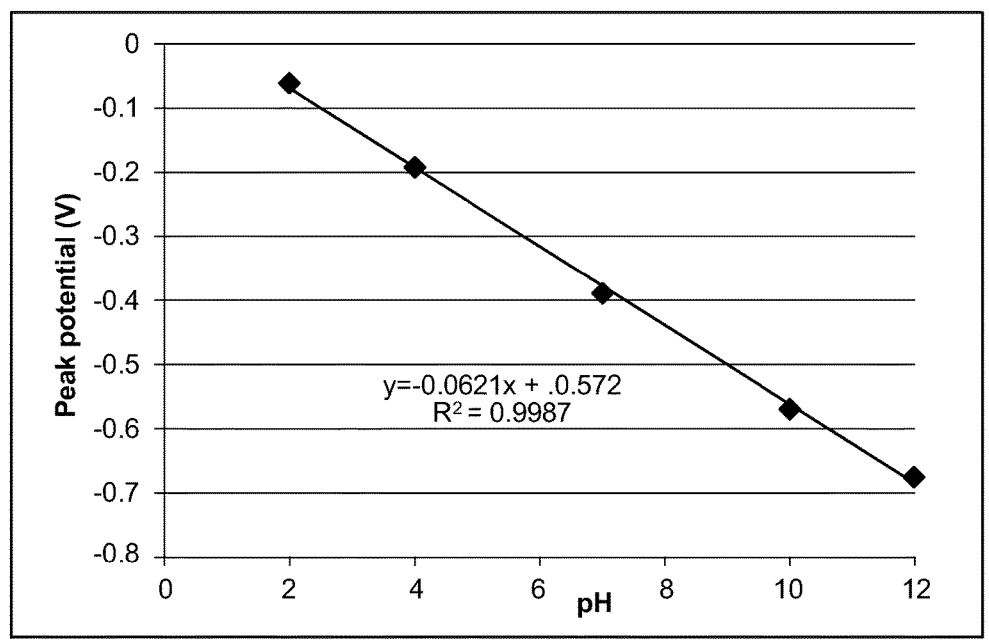
FIG. 12 is a graph displaying the potential at which current reached a maximum correlated linearly to the pH value of an analyte in accordance with a representative embodiment of the present invention.

The potential at which the current reached a maximum correlated linearly to the pH value of the analyte, as shown in FIG. 12. This relationship is characteristic of the chemical nature of the AQ-PVA described herein.

Example 2. 2-Methylanthraquinone Embedded in a Poly(Vinyl Alcohol) (PVA) Matrix and Working Electrodes Derived Therefrom This example illustrates the option of embedding an RAM in a polymer matrix where the RAM is not covalently bonded to the matrix. 2-methyl anthraquinone is a structurally similar analog of the 2-bromomethyl AQ used in Example 1.

Solutions of PVA (6 mg/mL, Alfa Aesar, low MW, 86-89% hydrolyzed), toluene-2,4-diisocyanate (TDI) (0.034 M, Aldrich T39853) and 2-methylanthraquinone (0.233 M) were prepared in DMSO. The 2-methylanthraquinone dissolved after heating to 50° C. with stirring. The materials were mixed by transferring 1 mL of the polymer solution to a glass vial and adding 50 µL of the TDI solution and 10 µL of the 2-methylanthraquinone. A 2 µL drop of the well-mixed solution was placed onto the tip of a prepared carbon fiber substrate. This working electrode was heated to 100° C. for 1 hour.

Square-wave voltammetry tests were conducted with this working electrode using standard buffer solutions. With a pH 7 buffer a current peak characteristic of AQ was observed at −536 mV with a signal intensity of 4.2 µA. This signal decreased by about one-third over the course of 17 hours. By comparison, a working electrode prepared with the AQ-PVA polymer described in Example 1 exhibited a peak at −504 mV and 21 µA, with no significant decay over 17 hours. These results showed that while it is possible to embed a RAM non-covalently to a matrix, with the potential of incremental improvements through process improvements, better performance is more readily achievable by means of covalent attachment of an analogous RAM.

Figure 13:
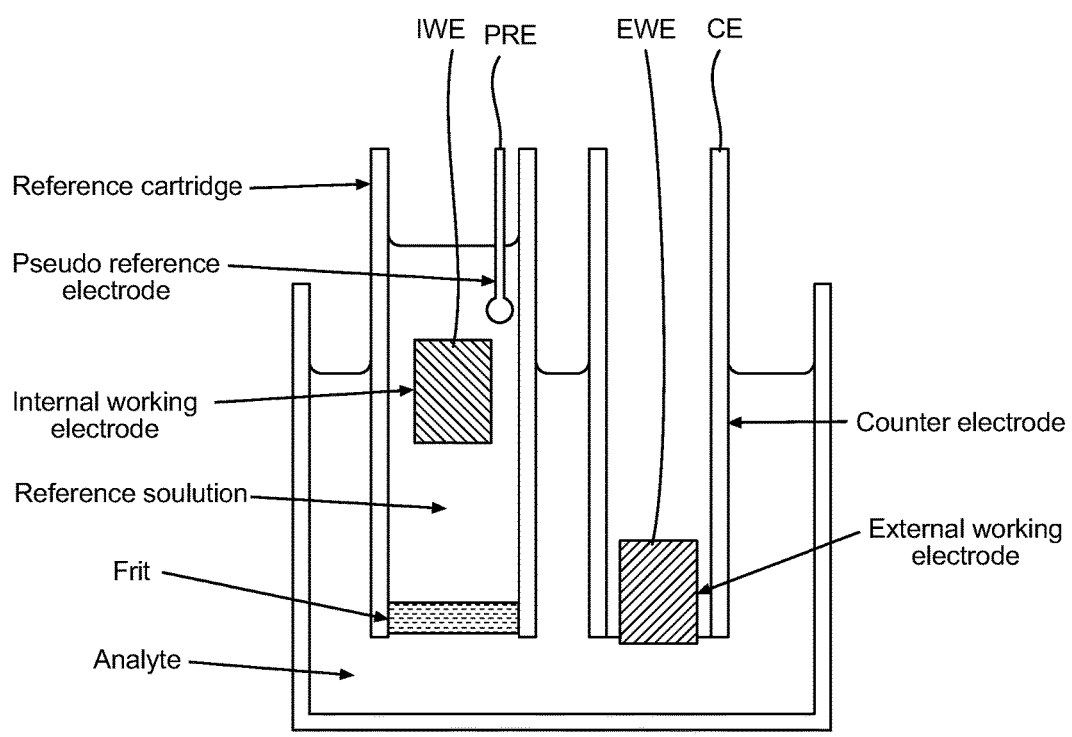
FIG. 13 is a schematic diagram of components of a voltammetric sensor system comprising an AIE reference electrode comprising a porous frit as a barrier between an analyte, a reference solution, a WE, and a CE in accordance with a representative embodiment of the present invention.

Example 3: An AIE Reference Electrode Comprising a Porous Frit as a Barrier Between Analyte and a Reference Solution An AIE reference electrode was prepared, as shown in FIG. 13. The AIE reference electrode contains various components, namely an Internal Working Electrode (IWE) which comprises a Working Electrode (WE) connected to a potentiostat (Metrohm Autolab PGSTAT12); a reference solution which fills the cartridge (i.e.: the cartridge is filled with pH 7 buffer (VWR Part #BDH5056) containing hydroxyethyl cellulose (Sigma Aldrich Part #434973) and KCl (Sigma Aldrich part #P3911) as additives; a pseudo reference electrode which comprises a silver wire located near the IWE and immersed in the reference solution; a frit which provides electrical contact with the analyte solution while restricting mass transfer between the reference solution and an analyte (i.e.: Porex POR-4902, 0.25" thick, 15-45 micrometer nominal pore size).

CE and EWE sensors were further prepared based upon a design described in PCT Pub. No. 2010/111531. The CE comprises a carbon fiber sleeve. The EWE is equivalent to the WE described in PCT Pub. No. 2010/111531. The IWE and EWE were constructed similarly, as described below, but may or may not differ in the analyte sensing material (ASM) used.

A Working Electrode of the current invention comprise a functionalized carbonaceous substrate surrounded by a polymeric sheath. For the illustrative example provided below, a carbon fiber substrate was encased concentrically in polyetheretherketone (PEEK). The end of the carbon fiber substrate was cut and polished in preparation for chemical treatment. A chemical treatment solution to attach the ASM to the carbonaceous substrate was prepared as follows: 1.5 mL of a 0.3 wt % solution of an adduct of anthraquinone and 3-aminopropyltrimethoxysilane (AQ-APTOS) in dichloromethane was added to a mixture of 3.5 mL ethanol, 250 mL of deionized water, 1.05 mL of tetraethylorthosilicate (TEOS), and 200 mL of 0.1 N hydrochloric acid. The reaction mixture was heated at 70° C. for 1 h. A solution of 0.27 g octyltrimethylammonium bromide (OTAB) in 6.5 mL ethanol was then added to the reaction mixture. Mixing was continued for an additional 30 min. The polished carbon substrate was briefly contacted with this chemical treatment solution, and then heated at 150° C. for 1 h. After cooling to ambient temperature, the WE was ready for use.

The IWE was maintained in a constant pH environment while the EWE was exposed directly to the analyte solution. For the tests described below, the CE and EWE were connected to a potentiostat.

The AIE reference electrode was tested using various external analyte. For example, various commercial buffer solutions were used, namely i) pH 2 Buffer (VWR part #BDH5012-20L); ii) pH 4 Buffer (VWR part #BDH5028-20L); iii) pH 7 Buffer (VWR part #BDH5056-20L); and iv) pH 10 Buffer (VWR part #BDH5082-20L).

Figure 14:
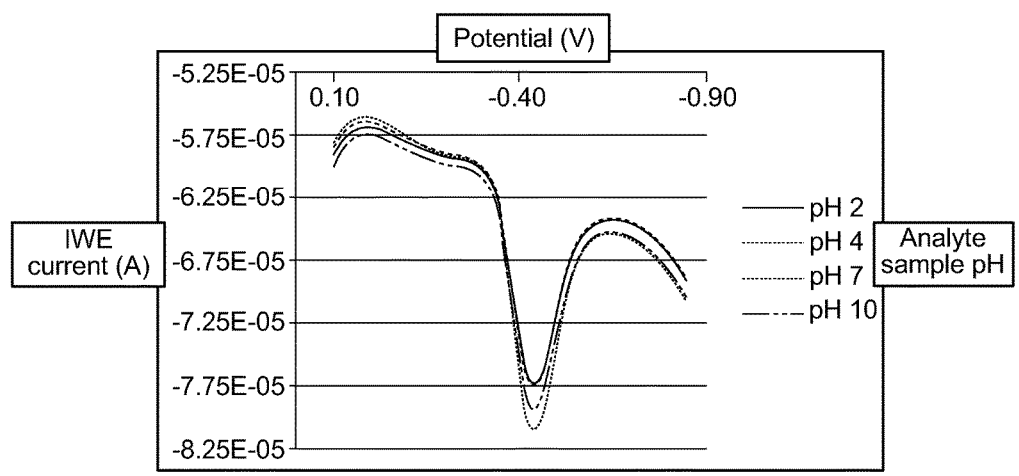
FIG. 14 is a graph displaying the results of a series of tests conducted on a potentiostat in various analyte solutions in accordance with a representative embodiment of the present invention.

A series of tests was conducted on the potentiostat including 10 square-wave scans in each of the analyte solutions (pH 2, 4, 7, and 10, all at 25° C.). The signals from the IWE are shown in FIG. 14.

Regardless of external analyte pH, the IWE displayed a peak position of −0.440V, which corresponds to pH 7. Continuing the test overnight using the pH 2 buffer as external analyte showed that the IWE peak position remained constant at −0.440V.

Figure 15:
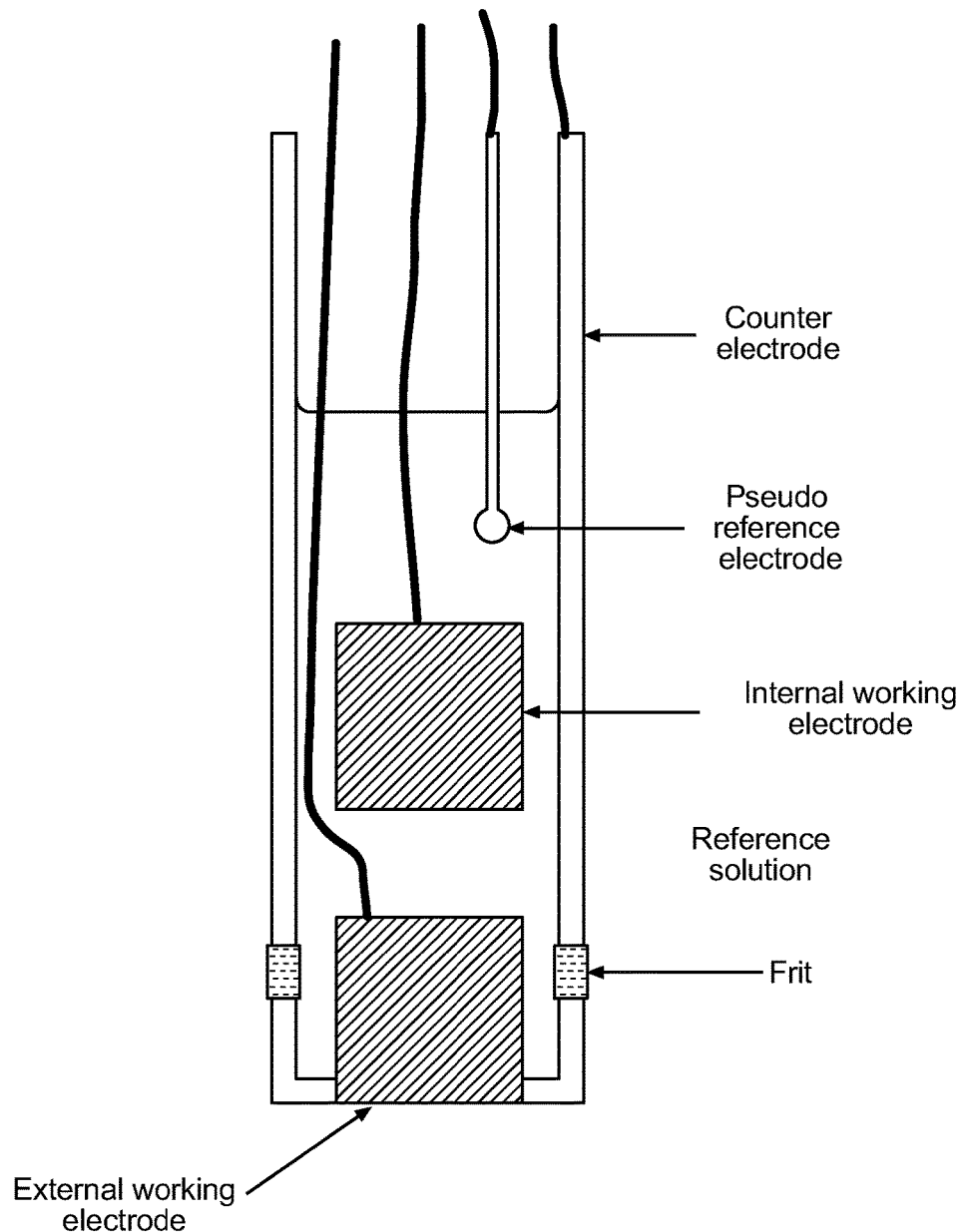
FIG. 15 is a schematic diagram of a voltammetric sensor cartridge combining a WE, CE, and an AIE (with IWE and PRE) reference electrode comprising a porous frit as a barrier between an analyte and a reference solution in accordance with a representative embodiment of the present invention.

Example 4: Design and Operation of a Voltammetric Sensor Cartridge Combining a WE, CE, and an AIE Reference Electrode (with IWE and PRE) Comprising a Porous Frit as a Barrier Between Analyte and Reference Solution A device with the design shown in FIG. 15 was constructed for pH measurements. The PRE comprised a silver wire (Alfa Aesar, Part #108U016); the CE was a carbon fiber tube (RockWest Composites, 12 mm OD); the IWE of the AIE and the WE (referred to in FIG. 15 as "external working electrode") were working electrodes prepared as described above. Different buffer solutions were used in the device as reference solution. In operation, the device was immersed in an analyte solution to a depth past the frit, and the signals from the IWE and EWE were monitored in the course of square wave voltammetry scans.

Figure 16:
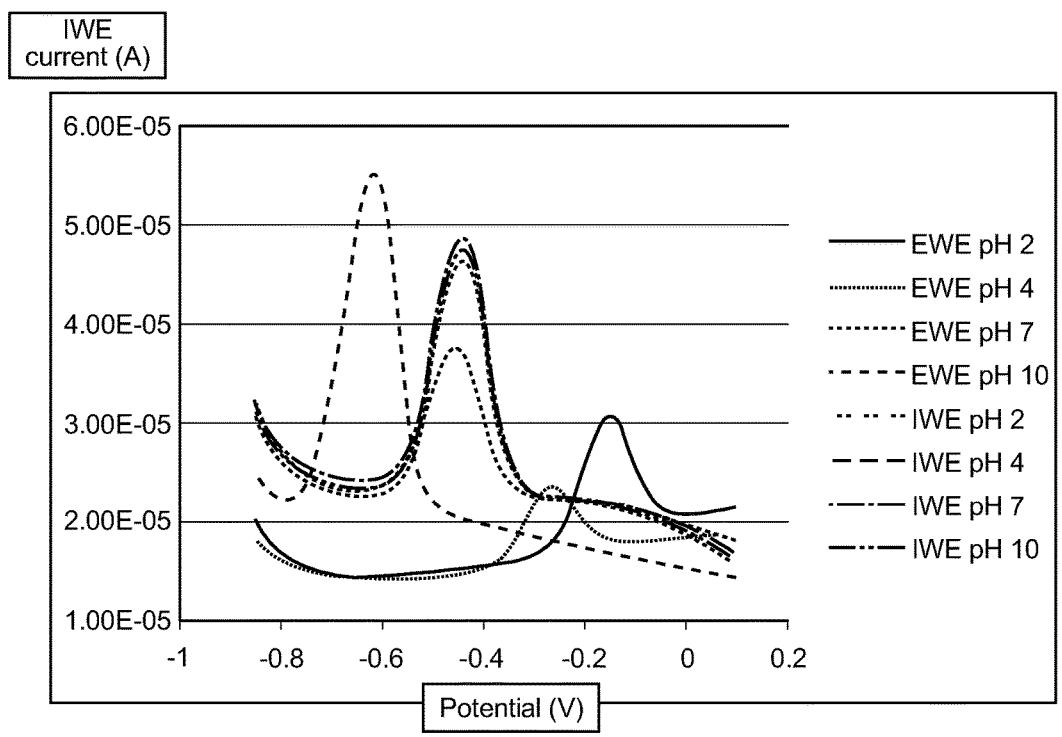
FIGS. 16-18 provide various tables and graphs which display results from tests conducted using a voltammetric sensor cartridge with various pH standard buffers as reference solutions and analyte solutions in accordance with a representative embodiment of the present invention.
Figure 17:
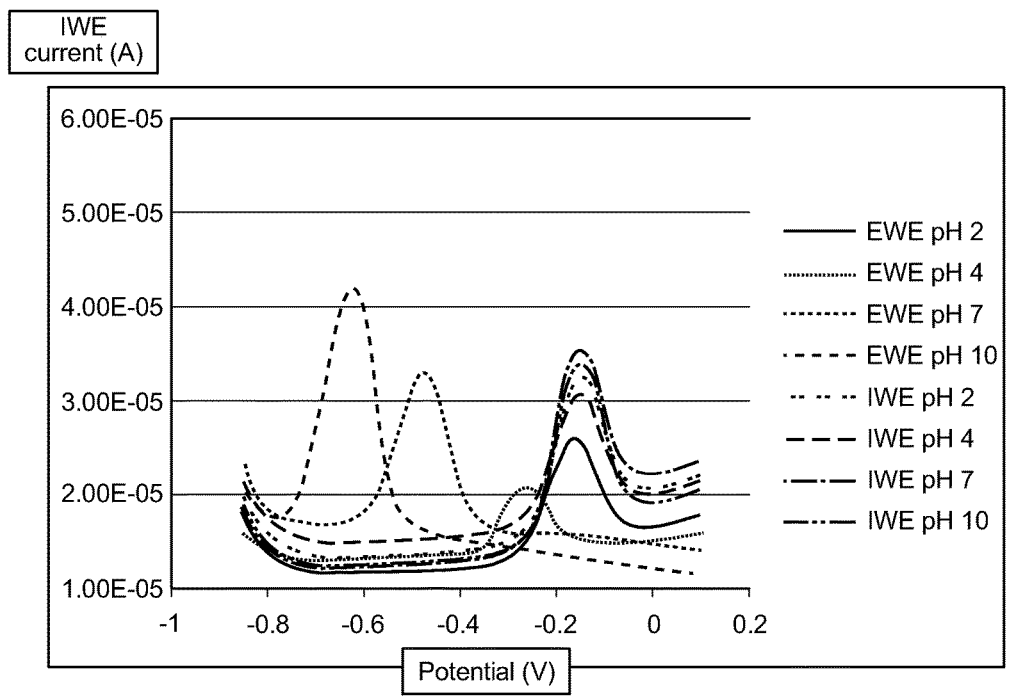
Figure 18:
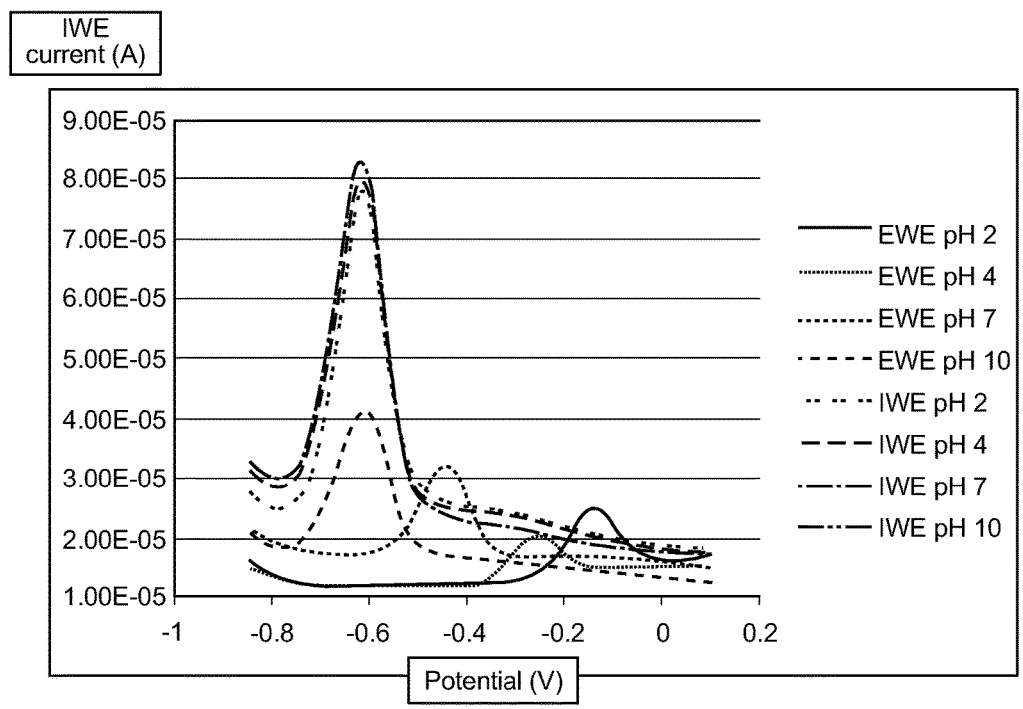

The following tests were conducted using pH 2, pH 7, and pH 10 standard buffers as the reference solution, and with pH 2, pH 7, and pH 10 buffers as analyte solutions. The peak positions associated with a given reference solution were recorded for the IWE and the EWE. The analyte pH was determined by taking the difference in peak potentials of the reference and buffer solutions. The results of these tests are shown in the tables and graphs of FIGS. 16-18 (PP denotes peak position in mV).

These results showed that in each of the reference solutions (pH 2, pH 7, and pH 10), the IWE signal peak position remained constant within ±2 mV (corresponding to 0.03 pH units) despite changes in analyte pH. Effectively the IWE exhibited an analyte-insensitivity over a broad pH range surpassing that of typical AIMs such as ferrocene. Meanwhile, the EWE exhibited the expected analyte sensitivity associated with the ASM used. In the present example, a 58 mV/pH correlation was observed with all reference solutions.

It is possible to sample the signals from the EWE and the IWE simultaneously in one current-potential scan, provided that the pH of the reference solution and the analyte solution are sufficiently different. If their pH values are similar, e.g. less than 0.5-1.0 pH unit, detection of individual peaks may be compromised by signal processing artifacts. Thus, in some embodiments of the methods for measuring pH provided by the invention, reference solutions are selected with pH values estimated to be about 2 pH units different from the anticipated analyte solution pH. The graph and chart shown in FIG. 19 shows the results of a test conducted with a reference solution comprising pH 1 buffer, and the analyte comprising a series of buffer solutions from pH 5 to pH 12.

Figure 19:
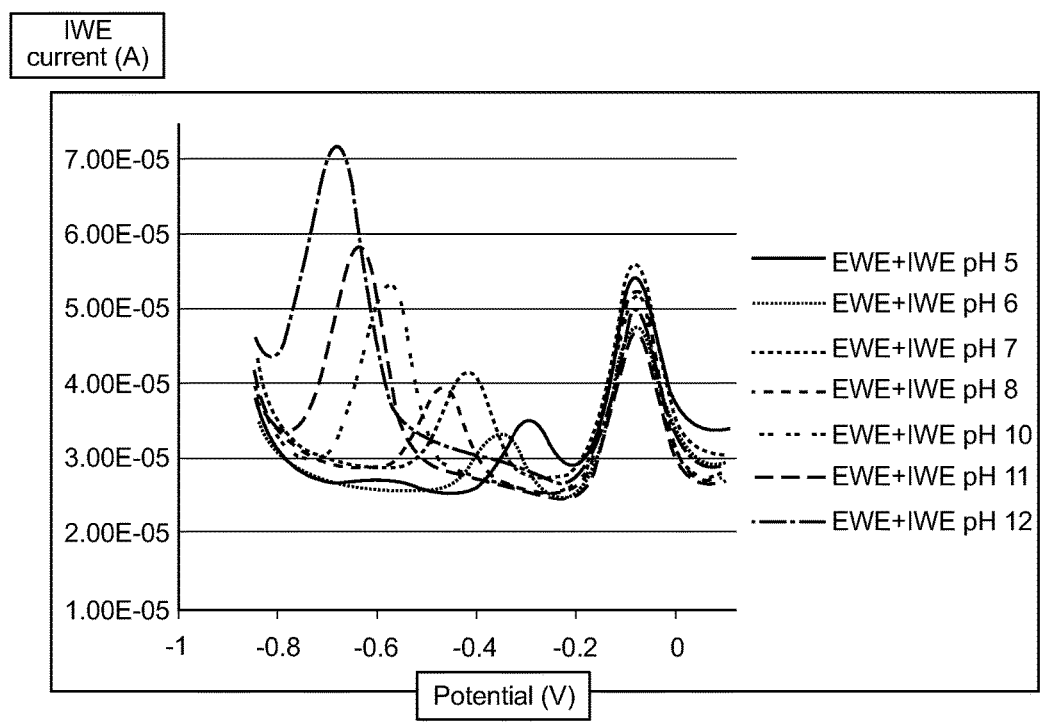
FIG. 19 provides a graph and chart displaying test results of a voltammetric sensor cartridge comprising a porous frit as a barrier between an analyte and a reference solution in accordance with a representative embodiment of the present invention.

With reference to the results shown in FIG. 19, the IWE peak position remained constant within 2 mV while the EWE correctly indicated the pH of the analyte solutions from pH 5 to pH 12.

In summary, the present invention provides, in one aspect, a pH probe based on ASM technology that does not utilize a conventional reference electrode typically used in commercial potentiometric pH electrodes. The test results presented here demonstrate that the invention provides a user calibration-free pH sensor. The test results presented here also demonstrate that the AIE of the invention is stable across a pH range from pH 2 to pH 12.

The use of different reference solutions for different analyte solutions is obviated if one measures the signals from the EWE and the IWE simultaneously using dual detection circuits, or by multiplexing the EWE and IWE signals through a single detection circuit. In this way, the signals from the EWE and the IWE are detected as non-overlapping peaks whose positions can be measured accurately, enabling even small differences in peak positions to be resolved reliably. Furthermore, an "all-purpose" reference solution may be used to cover a full range of analyte pH values. This reference solution can thus be optimized to be compatible chemically and electrochemically with the sensor components and other materials of construction in the pH probe.

Example 5: An AIE Reference Electrode with Wet-Dry Reversibility

Figures 20A, 20B:
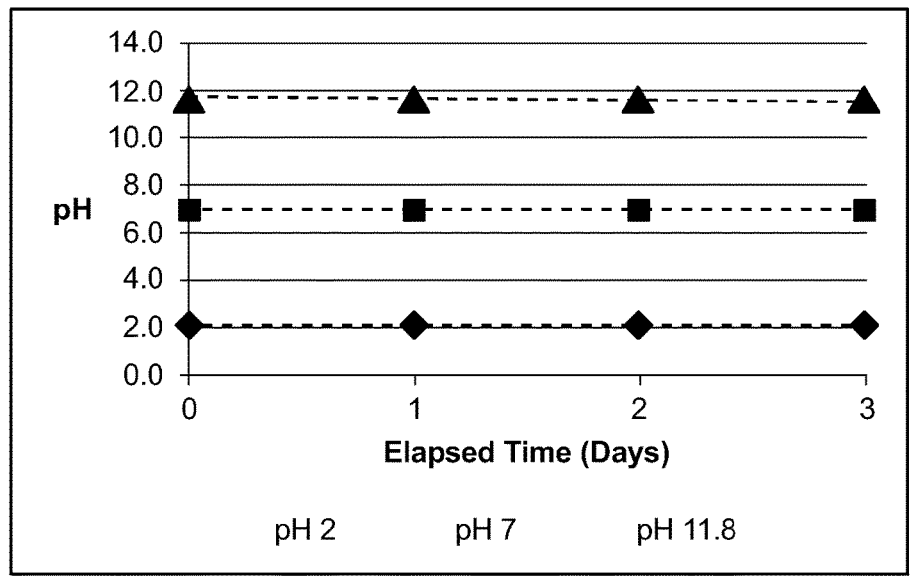
FIGS. 20A and 20B provide a graph and chart displaying test results of a reference electrode with wet-dry reversibility in accordance with a representative embodiment of the present invention.

An AIE reference electrode as described in Example 3 was constructed using a Nafion composite membrane in place of the frit. The Nafion composite membrane was prepared by imbibing a Nafion 117 solution in a microporous polyethersulfone membrane (EMD Millipore, 0.45 μm nominal pore size), and heat treated at 100° C. for 1 hour. The resultant membrane was cut to fit the open end of a tubing and sealed mechanically. The inside of the tube was filled with a 3M KCl solution containing hydroxymethylcellulose, and a chloridized silver wire was immersed in that thickened solution. The completed AIE reference electrode was tested using a WE fabricated in accordance with the procedure in Example 3, and a carbon fiber tube as CE. Testing was performed with pH 2, 7, and 12 BDH buffer solutions. Before beginning the tests, the RE was stored dry overnight. Measurement was made sequentially at pH 2, 7, and 12, followed by reversing the sequence, with intermediate rinses in deionized water. All tests are performed at ambient temperature. The sequence of measurements takes place over about 10 min. Additional test sequences are performed at 1-day intervals. Between tests the AIE reference electrode was left to dry in room air. Results shown in FIGS. 20A and 20B indicate that the AIE reference electrode remains fully functional after repeated drying.

Example 6: A Voltammetric Electrode Comprising a WE, a CE, and a Wet-Dry Reversible AIE Reference Electrode An AIE reference electrode was prepared as described in Example 5, except that a commercially available Nafion membrane was used instead of the Nafion/polyethersulfone membrane composite. An apparatus as described in Example 3 was assembled to conduct tests using various pH buffer solutions as analyte in contact with the EWE and the CE. A silver wire was used as PRE. A pH 1 buffer solution was used as reference solution. Results provided in FIGS. 21A-21C show a remarkably constant signal from the IWE even as the analyte pH was varied between 4 and 12. The relationship between analyte pH and the [IWE–EWE] peak potential difference was used to further calculate the pH of an unknown analyte.

This example describes a pH sensor system that combines the robustness of a non-glass electrode, stability associated with an internally-calibrated reference, and convenience of use that results from wet-dry reversibility.

Figure 8:
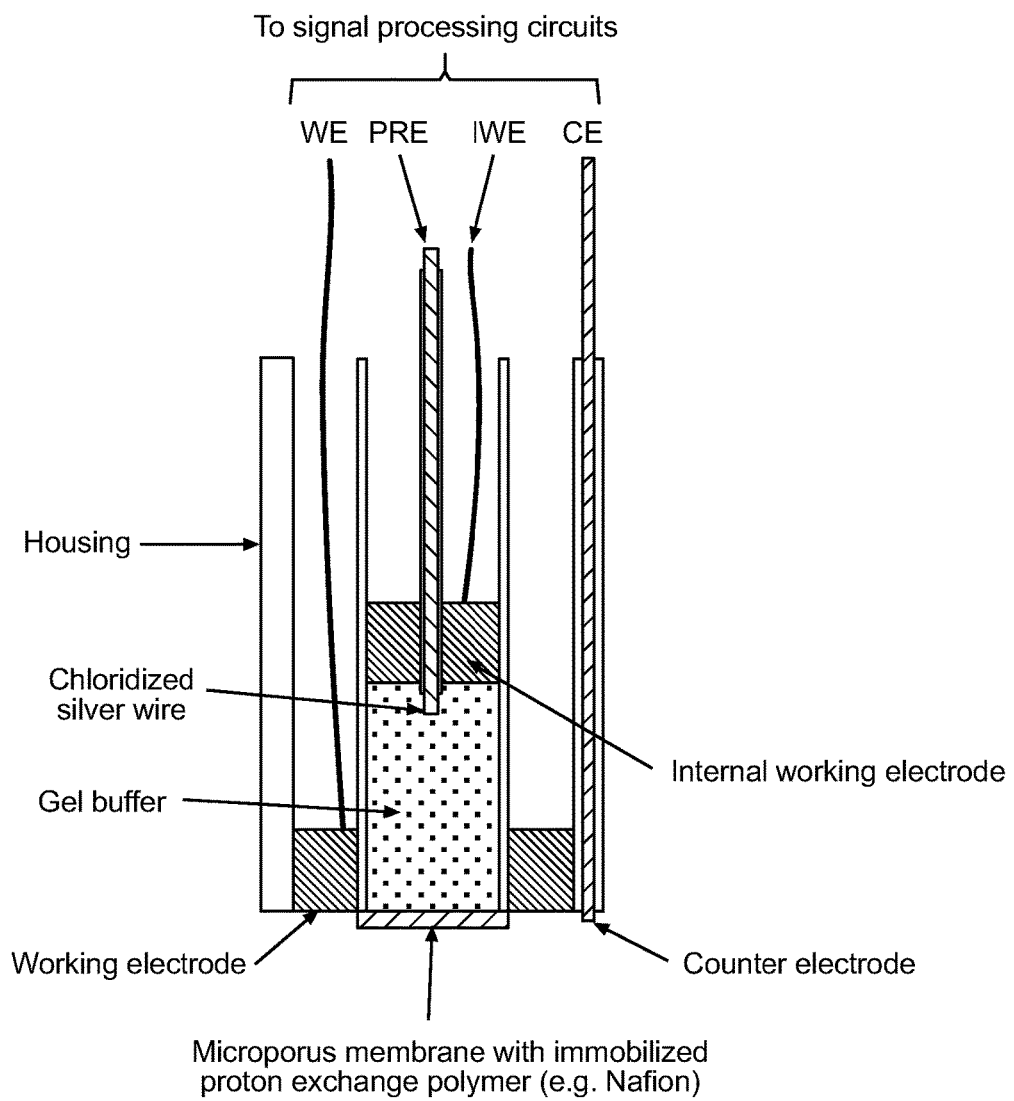
FIG. 8 is a schematic diagram of a voltammetric sensor comprising an AIE in accordance with a representative embodiment of the present invention.

Example 7: A Voltammetric Electrode Comprising a WE, a CE, and a Wet-Dry Reversible AIE Reference Electrode A cluster of sensors comprising a WE, a CE, and an AIE with the following spatial arrangement was constructed as described below to have the configuration shown in FIG. 8. The WE comprised a ring of polished carbon fiber substrate on the flat surface of which an ASM coating had been applied. The CE comprised an electroplated pin. The AIE comprised a Nafion composite membrane similar to that described in Example 5 above. The constant chemical environment (CCE) gel was formulated from a cross-linked polyacrylamide-based polymer, a pH 7 buffer, and glycerin. A chloridized silver wire formed the PRE. The IWE comprised a polished flat carbon fiber substrate on which an ASM coating had been applied. Conductive leads connect these sensor components to signal processing circuits. Thus integrated, the cluster of sensors was designed to perform the function of the apparatus described in Example 5 but in a single, housing with well-defined geometry and aspect ratio.

This cluster of sensors was tested using a series of buffer solutions from pH 2.04 to 11.65. Signals from the WE and the IWE were alternately measured, and the difference calculated as a function of the buffer solution pH. Results of these tests are shown in FIG. 22.

Figure 23:
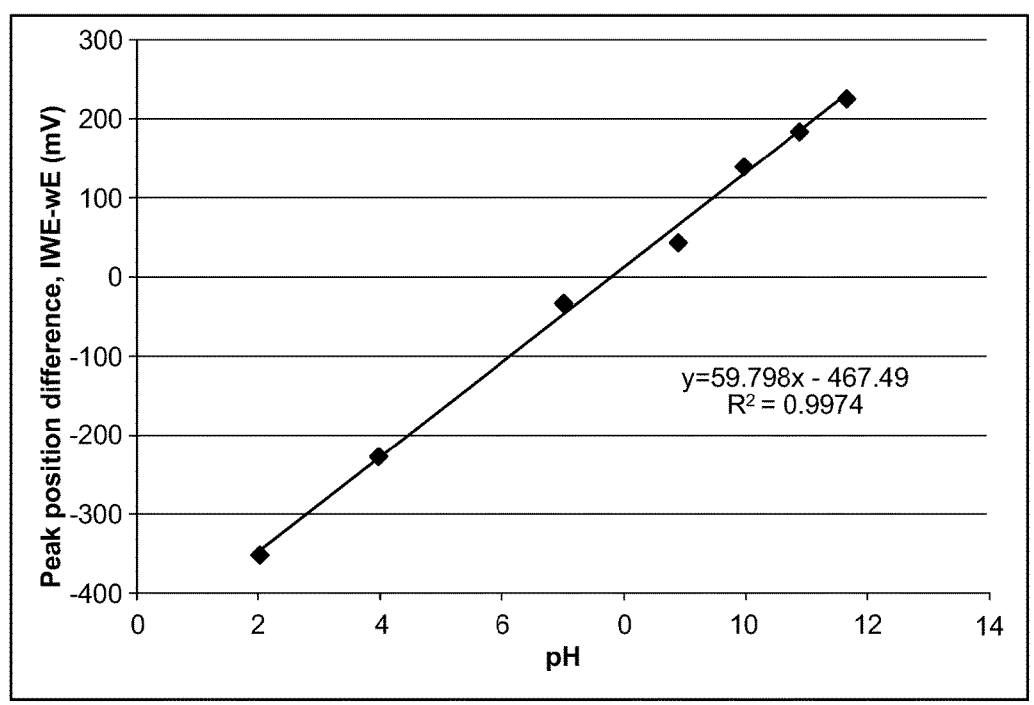
FIG. 23 is graph displaying the linear relationship between pH and [IWE−WE] in accordance with a representative embodiment of the present invention.

As expected of an AIE, the IWE signal remained constant despite changes in analyte pH. The relationship between pH and [IWE–WE] difference was virtually linear, as shown in FIG. 23. Accordingly, the cluster of sensors allowed direct pH determination of unknown analytes.

Figure 9:
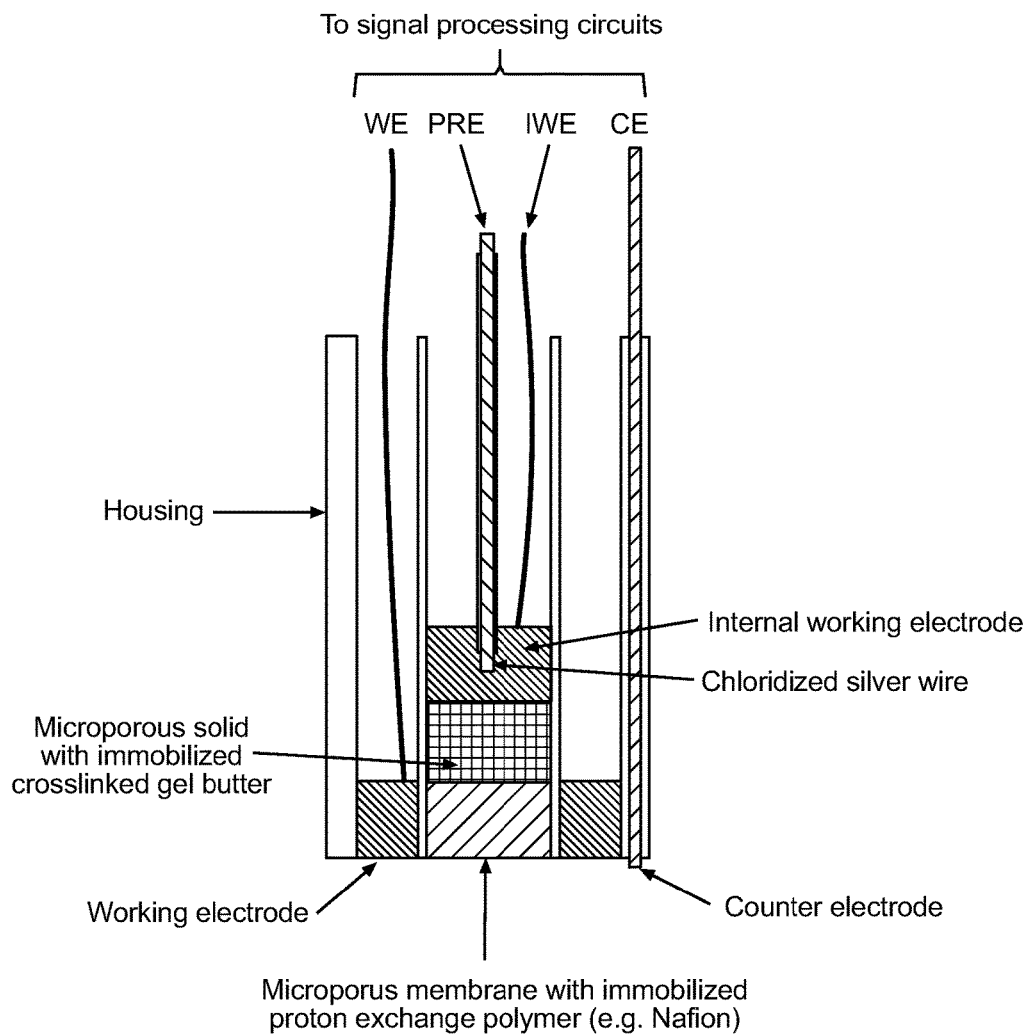
FIG. 9 is a schematic diagram of a voltammetric sensor comprising an alternate AIE in accordance with a representative embodiment of the present invention.

In other embodiments, as shown in FIG. 9, the cluster of sensors is constructed using rigid components, including the constant chemical environment which comprises a porous solid in which the CCE gel is immobilized. This construction adds to the robustness of the sensor.

What is claimed is:

1. A voltammetric sensor for use in conjunction with a pH meter, said voltammetric sensor-comprising:
    (i) a working electrode having a central opening;
    (i) an internal working electrode aligned with the central opening of the working electrode, said internal working electrode being non-covalently coated with a matrix material, said matrix material having an analyte sensitive material (ASM) or an analyte insensitive material (AIM) covalently attached thereto or non-covalently entrapped therein;
    (ii) a constant chemical environment aligned with and disposed within the central opening of the working electrode and interposed between the internal working electrode and the counter electrode and in contact with the ASM or AIM of the matrix material, and selected from the group consisting of a liquid, a semi-solid, and a solid comprising a buffer solution and at least one of:
        (a) a viscosity enhancer;
        (b) a gelling agent;
        (c) a zwitterionic polymer; and
        (d) an ionomer formulated to render a specific potential in conjunction with the internal working electrode;
    (iii) an analyte barrier aligned with the central opening of the working electrode, said constant chemical environment being interposedly positioned between said internal working electrode and said analyte barrier; and
    (iv) a pseudo reference electrode having a tip positioned in the constant chemical environment and a body passing through the internal working electrode.

2. The voltammetric sensor of claim 1, wherein the analyte barrier is an ionomer.

3. The voltammetric sensor of claim 1, wherein the analyte barrier is a sulfonated tetrafluoroethylene-based fluoropolymer-copolymer.

4. The voltammetric sensor of claim 1, wherein the analyte barrier is a solid that substantially prevents convective flow.

5. The voltammetric sensor of claim 2, wherein the ionomer is composed of Nafion (DuPont).

6. The voltammetric sensor of claim 1, wherein either or both of the constant chemical environment and the analyte barrier comprises a porous reinforcing matrix.

7. The voltammetric sensor of claim 1, wherein the pseudo-reference electrode, the internal working electrode, and the constant chemical environment are in the solid state.

8. The voltammetric sensor of claim 1 capable of wet-dry reversible operation.

9. A voltammetric sensor for use in conjunction with a pH meter, said voltammetric sensor comprising (i) components of the voltammetric sensor of claim 1; and (ii) electronic components and algorithm that convert an electronic signal output representing the measured pH value into a corresponding electrical potential that a pH meter can accept, process, display, and optionally further communicate with other computing devices, instrumentation and control systems.

10. The voltammetric sensor of claim 1, wherein the matrix material comprises a cross-linked polymer selected from the group consisting of a polyol, a poly(vinyl alcohol), a polysulfone, a polyethersulfone, a polyimide, a polysulfonamide, a polyimide, a polyester, a vinyl polymer, a polyphenylene sulfide, a polysaccharide, and cellulose.

11. The voltammetric sensor of claim 1, wherein the constant chemical environment comprises a zwitterionic polymer.

12. The voltammetric sensor of claim 1, wherein the analyte barrier is a zwitterionic polymer.

13. The voltammetric sensor of claim 1, wherein the constant chemical environment comprises an ionomer formulated to render a specific potential in conjunction with the internal working electrode.

* * * * *